(12) United States Patent
Minamisawa et al.

(10) Patent No.: US 10,259,889 B2
(45) Date of Patent: Apr. 16, 2019

(54) METHOD FOR SULFATING GLYCOSAMINOGLYCAN

(71) Applicant: SEIKAGAKU CORPORATION, Tokyo (JP)

(72) Inventors: Toshikazu Minamisawa, Tokyo (JP); Nagamasa Asami, Tokyo (JP); Hiroshi Fujita, Tokyo (JP); Kiyoshi Suzuki, Tokyo (JP)

(73) Assignee: SEIKAGAKU CORPORATION, Tokyo (JP)

( * ) Notice: Subject to any disclaimer, the term of this patent is extended or adjusted under 35 U.S.C. 154(b) by 0 days.

(21) Appl. No.: 15/563,196

(22) PCT Filed: Mar. 31, 2016

(86) PCT No.: PCT/JP2016/060788
§ 371 (c)(1),
(2) Date: Sep. 29, 2017

(87) PCT Pub. No.: WO2016/159296
PCT Pub. Date: Oct. 6, 2016

(65) Prior Publication Data
US 2018/0086853 A1 Mar. 29, 2018

(30) Foreign Application Priority Data
Mar. 31, 2015 (JP) .................. 2015-073148

(51) Int. Cl.
C08B 37/00 (2006.01)
(52) U.S. Cl.
CPC .......... *C08B 37/0075* (2013.01); *C08B 37/00* (2013.01); *C08B 37/0069* (2013.01)
(58) Field of Classification Search
None
See application file for complete search history.

(56) References Cited

U.S. PATENT DOCUMENTS

| | | | |
|---|---|---|---|
| 5,008,253 A | 4/1991 | Casu et al. | |
| 5,013,724 A | 5/1991 | Petitou et al. | |
| 5,384,398 A | 1/1995 | Lormeau et al. | |
| 6,388,060 B1 | 5/2002 | Guo et al. | |
| 2005/0233453 A1 | 10/2005 | Kariya et al. | |
| 2011/0244520 A1 | 10/2011 | Doherty et al. | |
| 2014/0296505 A1 | 10/2014 | Doherty et al. | |

FOREIGN PATENT DOCUMENTS

| | | |
|---|---|---|
| EP | 0 340 628 A2 | 11/1989 |
| JP | 38-025652 B1 | 12/1963 |
| JP | 62-027402 A | 2/1987 |
| JP | 1-318002 A | 12/1989 |
| JP | 9-168384 A | 6/1997 |
| JP | 11-12137 A | 1/1999 |
| JP | 11-147901 A | 6/1999 |
| JP | 2001-097997 A | 4/2001 |
| JP | 2003-268004 A | 9/2003 |
| JP | 2005-290383 A | 10/2005 |
| JP | 2007-016099 A | 1/2007 |
| JP | 2008-174642 A | 7/2008 |
| JP | 2013-520995 A | 6/2013 |
| WO | 95/25751 A1 | 9/1995 |
| WO | 2006/101000 A1 | 9/2006 |

OTHER PUBLICATIONS

Varsha D. Nadkarni, et al. "Preparation and biological activity of N-sulfonated chondroitin and dermatan sulfate derivatives", Carbohydrate Research, 1996, pp. 87-96, vol. 290.
Daria Leali, et al., "Fibroblast Growth Factor-2 Antagonist Activity and Angiostatic Capacity of Sulfated *Escherichia coli* K5 Polysaccharide Derivatives", The Journal of Biological Chemistry, Oct. 12, 2001, pp. 37900-37908, vol. 276, No. 41.
Sumit Bhattacharyya, et al., "Cell-Bound IL-8 Increases in Bronchial Epithelial Cells after Arylsulfatase B Silencing due to Sequestration with Chondroitin-4-Sulfate", American Journal of Respiratory Cell and Molecular Biology, 2010, pp. 51-61, vol. 42.
Daniel J. Rigden, et al., "Structures of *Streptococcus pneumoniae* Hyaluronate Lyase in Complex with Chondroitin and Chondroitin Sulfate Disaccharides", The Journal of Biological Chemistry, 2003, pp. 50596-50606, vol. 278, No. 50.
K. Fuller, et. al., "Heparin Augments Osteoclast Resorption-Stimulating Activity in Serum", Journal of Cellular Physiology, 1991, pp. 208-214, vol. 147.
Vera Hintze, et. al., "Sulfated Glycosaminoglycans Exploit the Conformational Plasticity of Bone Morphogenetic Protein-2 (BMP-2) and Alter the Interaction Profile with Its Receptor", bioMacromolecules, 2014, pp. 3083-3092, vol. 15.
International Search Report for PCT/JP2016/060788 dated Jul. 5, 2016 [PCT/ISA/210].
International Preliminary Report on Patentability issued from the International Bureau in counterpart International Application No. PCT/JP2016/060788, dated Oct. 12, 2017.
Extended European Search Report, dated Nov. 16, 2018, issued by the European Patent Office in counterpart European Patent Application No. 16773176.9.

*Primary Examiner* — Layla D Berry
(74) *Attorney, Agent, or Firm* — Sughrue Mion, PLLC

(57) ABSTRACT

An object of the present invention is provide a method for sulfating a glycosaminoglycan in a solution of a non-organic solvent. In the present invention, sulfation reaction of a glycosaminoglycan is performed with a sulfating agent in a strongly basic solution of a non-organic solvent. In the present invention, pH of the strongly basic solution is preferably set to be 11.5 or higher. According to the present invention, for example, a glycosaminoglycan having heparin-like anticoagulant activity can be produced from N-acetylheparosan through one-pot procedure. In one embodiment, a sulfated glycosaminoglycan produced by the method of the present invention has a unique disaccharide composition and is expected to be a novel useful material.

13 Claims, 3 Drawing Sheets

METHOD FOR SULFATING GLYCOSAMINOGLYCAN

CROSS REFERENCE TO RELATED APPLICATIONS

This application is a National Stage of International Application No. PCT/JP2016/060788, filed Mar. 31, 2016, which claims priority to Japanese Patent Application No. 2015-073148, filed Mar. 31, 2015, the contents of all of which are incorporated herein by reference in their entirety.

TECHNICAL FIELD

The present invention relates to, for example, a method for sulfating a glycosaminoglycan.

BACKGROUND ART

The following abbreviations are used in the present specification.
GAG: glycosaminoglycan
HexN: hexosamine
HexNAc: N-acetylhexosamine
GalN: galactosamine
GalNAc: N-acetylgalactosamine
GlcN: glucosamine
GlcNAc: N-acetylglucosamine
GlcNS: N-sulfoglucosamine
HexA: hexuronic acid
GlcA: glucuronic acid
IdoA: iduronic acid
ΔHexA: unsaturated hex conic acid
CS: chondroitin sulfate
DS: dermatan sulfate
CH: chondroitin
dCH: desulfated chondroitin sulfate
HA: hyaluronic acid
HPN: heparosan
NAH: N-acetylheparosan
HS: heparan sulfate
HEP: heparin
dHEP: desulfated heparin
AS: acharan sulfate
ACH: acharan (2-O-desulfated AS)
KS: keratan sulfate
KPS: keratan polysulfate
ΔDi-0S: ΔHexAα1-3GalNAc
ΔDi-6S: ΔHexAα1-3GalNAc(6S)
ΔDi-4S: ΔHexAα1-3GalNAc(4S)
ΔDi-2S: ΔHexA(2S)α1-3GalNAc
ΔDi-diS$_D$: ΔHexA(2S)α1-3GalNAc(6S)
ΔDi-diS$_E$: ΔHexAα1-3GalNAc(4S,6S)
ΔDi-diS$_B$: ΔHexA(2S)α1-3GalNAc(4S)
ΔDi-triS: ΔHexA(2S)α1-3GalNAc(4S,6S)
ΔDiHA-0S: ΔHexAα1-3GlcNAc
ΔDiHA-6S: ΔHexAα1-3GlcNAc(6S)
ΔDiHA-4S: ΔHexAα1-3GlcNAc(4S)
ΔDiHA-2S: ΔHexA (2S)α1-3GlcNAc
ΔDiHS-0S: ΔHexAα1-4GlcNAc
ΔDiHS-NS: ΔHexAα1-4GlcNS
ΔDiHS-6S: ΔHexAα1-4GlcNAc(65)
ΔDiHS-2S: ΔHexA(2S)α1-4GlcNAc
ΔDiHS-diS$_1$: ΔHexAα1-4Glc(NS, 6S)
ΔDiHS-diS$_2$: ΔHexA(2S)α1-4GlcNS
ΔDiHS-diS$_3$: ΔHexA(2S)α1-4GlcNAc(6S)
ΔDiHS-triS: ΔHexA(2S)α1-4Glc(NS,6S)

In the above description, "α1-3" refers to an α1-3 glycosidic bond, "α1-4" an α1-4 glycosidic bond, "6S" a 6-O-sulfate group, "4S" a 4-O-sulfate group, and "2S" a 2-O-sulfate group, respectively.

Known techniques for sulfating a glycosaminoglycan (GAG) include chemical synthesis, enzymatic synthesis, and a combination thereof (i.e., chemo-enzymatic synthesis). A known method for sulfating a hydroxy group of a GAG (O-sulfation method) through chemical synthesis involves the use of an organic solvent. A known O-sulfation method involves conversion of a GAG into a quaternary ammonium salt form, dissolution of the GAG salt in an organic solvent, and addition of a sulfating agent to the solution for O-sulfation, for example, dissolution of tributylamine salt of N-acetylheparosan in N,N-dimethylformamide, and addition of a sulfur trioxide-pyridine complex to the solution for O-sulfation (Patent Document 1). Another known O-sulfation method involves dissolution of a GAG in a polar organic solvent, and addition of a sulfating agent to the solution for O-sulfation; for example, dissolution of chondroitin in formamide, and addition of a sulfur trioxide-triethylamine complex to the solution for O-sulfation (Patent Document 2). In a method using an organic solvent, the sulfation reaction is terminated by, for example, addition of an aqueous solution containing a salt for pH adjustment (e.g., sodium acetate), since the sulfating agent is inactivated by water (Patent Document 2).

A known method for sulfating an amino group of a GAG (N-sulfation method) through chemical synthesis involves dissolution of an N-deacetylated GAG in a weakly basic aqueous solution having a pH of about 10 (e.g., an aqueous sodium carbonate solution or an aqueous sodium hydrogen carbonate solution), and addition of a sulfating agent to the solution for N-sulfation. Examples of known N-sulfation methods include a method involving N-deacetylation of chondroitin sulfate by hydrazine decomposition, dissolution of the N-deacetylated product in an aqueous sodium carbonate solution, and addition of a sulfur trioxide-triethylamine complex to the solution for N-sulfation; and a method involving N-deacetylation of N-acetylheparosan (K5 polysaccharide) by alkaline hydrolysis, neutralization of the N-deacetylated product, and addition of sodium carbonate and a sulfur trioxide-pyridine complex to the neutralized product for N-sulfation (Non-Patent Documents 1 and 2). However, such a method involving sulfation reaction in a weakly basic aqueous solution specifically sulfates an amino group of a GAG, and fails to sulfate a hydroxy group of a GAG.

PRIOR ART DOCUMENTS

Patent Documents

Patent Document 1: Japanese Patent Application Laid-Open (kokai) No. 2005-290383
Patent Document 2: Japanese Kohyo (PCT) Patent Publication No. 2013-520995

Non-Patent Documents

Non-Patent Document 1: Nadkarni V D, Toida T, Van Gorp C L, Schubert R L, Weiler J M, Hansen K P, Caldwell E E, Linhardt R J., Carbohydr. Res. 1996 Aug. 26; 290(1): 87-96
Non-Patent Document 2: Leali D, Belleri M, Urbinati C, Coltrini D, Oreste P, Zoppetti G, Ribatti D, Rusnati M, Presta M., J. Biol. Chem. 2001 Oct. 12; 276(41): 37900-8

SUMMARY OF THE INVENTION

Problems to be Solved by the Invention

In view of the aforementioned sulfation method (i.e., the use of an organic solvent for chemical sulfation of a hydroxy group of a GAG), the present inventors have conducted extensive studies on a method for sulfating a GAG by use of a reduced amount of an organic solvent (preferably without use of an organic solvent) from the viewpoint of green and sustainable chemistry.

An object of the present invention is provide a method for sulfating a GAG in a solution of a non-organic solvent. In one embodiment, an object of the present invention is to provide a method for sulfating a hydroxy group of a GAG in a solution of a non-organic solvent.

Means for Solving the Problems

The present inventors have conducted extensive studies for solving the aforementioned problems, and as a result have found that a hydroxy group of a GAG can be sulfated, without use of an organic solvent, by a method involving sulfation reaction in a strongly basic solution (alkaline solution) under coexistence of the GAG with a sulfating agent (i.e., a method by use of an aqueous solvent). The present inventors have also found that a sulfated GAG prepared by the method has, in one embodiment, new disaccharide composition; i.e., disaccharide composition different from that of a sulfated GAG prepared through sulfation in an organic solvent or a GAG extracted from an animal. The present inventors have accomplished the present invention on the basis of these findings.

Accordingly, the present invention, which solves the aforementioned problems, includes the following embodiments.

[1]
A method for sulfating a glycosaminoglycan, the method comprising performing sulfation reaction in a strongly basic solution under coexistence of a glycosaminoglycan with a sulfating agent.

[2]
The method according to [1] above, wherein pH of the strongly basic solution is set to be 11.5 or higher.

[3]
The method according to [1] or [2] above, wherein the strongly basic solution contains a strong base.

[4]
The method according to any of [1] to [3] above, wherein the glycosaminoglycan is selected from among the following glycosaminoglycans (A) to (D):
(A) a glycosaminoglycan having a hexuronic acid residue;
(B) a glycosaminoglycan prepared through addition or elimination of a substituent or a functional group to or from the glycosaminoglycan (A);
(C) a glycosaminoglycan prepared through deacetylation of the glycosaminoglycan (A); and
(D) a glycosaminoglycan prepared through alkylation of the glycosaminoglycan (A).

[5]
The method according to any of [1] to [4] above, wherein the sulfating agent is a sulfur trioxide complex.

[6]
A method for producing a sulfated glycosaminoglycan, the method comprising a step of performing a method as recited in any of [1] to [5] above.

[7]
The method according to [6] above, the method further comprising a step of performing deacetylation reaction of the glycosaminoglycan.

[8]
The method according to [6] or [7] above, the method further comprising a step of performing alkylation reaction of the glycosaminoglycan.

[9]
Chondroitin sulfate containing 3 mol % or higher of a disaccharide having a structure represented by the following formula as the composition ratio of disaccharide units:

[HexA(2S)1-3GalN1-4]

(where "HexA" represents a hexuronic acid residue; "GalN" represents a galactosamine residue; "1-3" represents a 1-3 glycosidic bond; "1-4" represents a 1-4 glycosidic bond; and "2S" represents a 2-O-sulfate group, respectively).

[10]
Chondroitin sulfate containing a disaccharide having a structure represented by the following formula (b) over 3 times as many as a disaccharide having a structure represented by the following formula (a):

[HexA1-3GalN(4S)1-4]    (a)

[HexA(2S)1-3GalN1-4]    (b)

(where "HexA" represents a hexuronic acid residue; "GalN" represents a galactosamine residue; "1-3" represents a 1-3 glycosidic bond; "1-4" represents a 1-4 glycosidic bond; "4S" represents a 4-O-sulfate group; and "2S" represents a 2-O-sulfate group, respectively).

[11]
Chondroitin sulfate containing a disaccharide having a structure represented by the following formula (d) over 0.1 times as many as a disaccharide having a structure represented by the following formula (c):

[HexA1-3GalN(6S)1-4]    (c)

[HexA(2S)1-3GalN1-4]    (d)

(where "HexA" represents a hexuronic acid residue; "GalN" represents a galactosamine residue; "1-3" represents a 1-3 glycosidic bond; "1-4" represents a 1-4 glycosidic bond; "6S" represents a 6-O-sulfate group; and "2S" represents a 2-O-sulfate group, respectively).

[12]
Chondroitin sulfate having 25 mol % or higher of a disaccharide having a structure represented by the following formula as the composition ratio of disaccharide units:

[HexA(2S)1-3GalN(6S)1-4]

(where "HexA" represents a hexuronic acid residue; "GalN" represents a galactosamine residue; "1-3" represents a 1-3 glycosidic bond; "1-4" represents a 1-4 glycosidic bond; "2S" represents a 2-O-sulfate group; and "6S" represents a 6-O-sulfate group, respectively).

[13]
Sulfated hyaluronic acid containing a disaccharide having a structure represented by the following formula as the disaccharide composition:

[HexA1-3GlcN(4S)1-4]

(where "HexA" represents a hexuronic acid residue; "GlcN" represents a glucosamine residue; "1-3" represents a 1-3 glycosidic bond; "1-4" represents a 1-4 glycosidic bond; and "4S" represents a 4-O-sulfate group, respectively).

[14]
Sulfated hyaluronic acid having the following characteristics (A) and (B):
(A) a molecular weight of 2,000,000 Da or higher, and
(B) a sulfur content of 2 mass % or higher.
[15]
The method according to any of [6] to [8] above, wherein the sulfated glycosaminoglycan has heparin-like anticoagulant activity.
[16]
The method according to any of [6] to [8] above, wherein the sulfated glycosaminoglycan is sulfated heparosan having heparin-like anticoagulant activity.
[17]
The method according to any of [6] to [8] above, wherein the sulfated glycosaminoglycan is chondroitin sulfate as recited in any of [9] to [12] above or sulfated hyaluronic acid as recited in [13] or [14] above.
[18]
The method according to any of [6] to [8] above, wherein the sulfated glycosaminoglycan is chondroitin sulfate as recited in [9], [10], [11], and/or [12] above.
[19]
The method according to any of [6] to [8] above, wherein the sulfated glycosaminoglycan is sulfated hyaluronic acid as recited in [13] and/or [14] above.

Advantageous Effects of the Invention

According to the present invention, a GAG can be sulfated in a solution of a non-organic solvent. According to the present invention, a hydroxy group of a GAG can be sulfated in a solution of a non-organic solvent,

Figure 1:
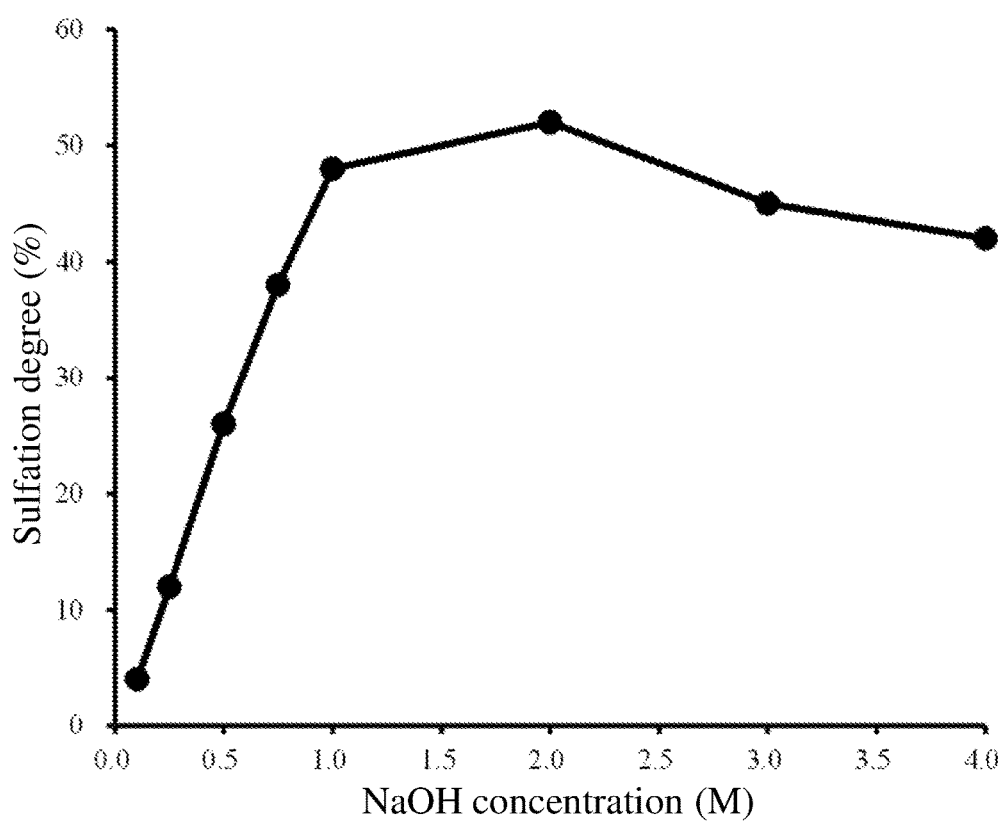
FIG. 1 A graph illustrating the relationship between NaOH concentration and the sulfation degree in sulfated CH prepared through coexistence of C: with a sulfur trioxide-trimethylamine complex (TMA-SO$_3$) in an aqueous NaOH solution.

MODES FOR CARRYING OUT THE INVENTION (1) Sulfation Method of the Present Invention As described above, the present invention provides a method for sulfating a GAG, the method being characterized by comprising performing sulfation reaction of a GAG in a solution of a non-organic solvent under coexistence of the GAG with a sulfating agent (hereinafter the method referred to as "the sulfation method of the present invention"). As used herein, the term "non-organic solvent" refers to a solvent including a solvent other than an organic solvent (e.g., an inorganic solvent). The "solution of a non-organic solvent" as used herein is, specifically, a strongly basic solution. In the sulfation method of the present invention, pH of the strongly basic solution is preferably set to be 11.5 or higher, in the sulfation method of the present invention, pH of the strongly basic solution may be set to be 11.6 or higher, 11.8 or higher, 12 or higher, 12.2 or higher, 12.4 or higher, 12.6 or higher, 12.8 or higher, or 13 or higher.

In the sulfation method of the present invention, the sulfation reaction can be performed in a strongly basic solution under coexistence of a GAG with a sulfating agent. As used herein, the term "coexistence" refers to a state where substances of interest can come into contact with each other. Thus, the sulfation reaction can be performed by, for example, adding a sulfation agent to a strongly basic solution containing a GAG; adding a GAG to a strongly basic solution containing a sulfating agent; or changing a solution containing a GAG and a sulfating agent into strongly basic condition. The sulfation reaction can proceed within a period of time during which a GAG coexists with a sulfating agent, so long as the solution containing the GAG and the sulfating agent exhibits strong basicity within the period of time. The solution does not necessarily constantly exhibit strong basicity within the period of time. In some embodiments of the sulfation method of the present invention, the pH of the solution may vary within the period of time during which the GAG coexists with the sulfating agent, depending on, for example, the type or amount of the sulfating agent. Even in such a case, the GAG can be sulfated by the sulfation method of the present invention, so long as the solution exhibits strong basicity within the below-described period of time for the sulfation reaction during a time the GAG coexists with the sulfating agent.

The strongly basic solution may be a solution of a non-organic solvent. Specifically, the strongly basic solution may be a solution of an inorganic solvent, or a solution of a mixture of an inorganic solvent and an organic solvent. No particular limitation is imposed on the organic solvent, but the organic solvent is preferably miscible with an inorganic solvent. Example of such an organic solvent includes a polar organic solvent. The polar organic solvent may be an aprotic polar solvent or a protic polar solvent. The polar organic solvent is preferably an aprotic polar solvent. Examples of the polar organic solvent include alcohols (e.g., ethanol), dimethyl sulfoxide, N,N-dimethylformamide, formamide, tetrahydrofuran, pyridine, acetone, and acetonitrile. No particular limitation is imposed on the inorganic solvent, but the inorganic solvent is preferably a neutral or basic solvent. Example of the inorganic solvent includes an aqueous solvent (e.g., water). Thus, in one embodiment, the strongly basic solution may be a strongly basic aqueous solution. No particular limitation is imposed on the amount (volume) of the strongly basic solution used for the sulfation reaction, and the amount of the solution can be appropriately determined depending on, for example, the amount of the GAG or sulfating agent used.

In the sulfation method of the present invention, the solution used for the sulfation reaction (hereinafter referred to as "sulfation reaction solution") may be a solution containing an organic solvent or a solution containing no organic solvent. No particular limitation is imposed on the amount of the organic solvent contained in the sulfation reaction solution, and the amount of the organic solvent can be appropriately determined depending on various conditions, such as the type of the organic solvent and the desired degree of sulfation. In the sulfation method of the present invention, the organic solvent can be used so that, for example, the volume concentration (v/v) of the organic solvent contained in the sulfation reaction solution falls within the range described below. The volume concentration of the organic solvent may be higher than 0%. The volume concentration of the organic solvent may be, for example, 0.001% or higher, 0.01% or higher, 0.1% or higher, 1% or higher, or 5% or higher. The volume concentration of the organic solvent may be, for example, 99% or lower, 80% or lower, 60% or lower, 40% or lower, 20% or lower, 10% or lower, 5% or lower. The volume concentration of the organic solvent is preferably, for example, higher than 0% and 99% or lower, higher than 0% and 80% or lower, higher than 0% and 60% or lower, higher than 0% and 40% or lower, higher than 0% and 20% or lower, higher than 0% and 10% or lower, or higher than 0% and 5% or lower. Only one kind of organic solvent may be used, or two or more kinds of organic solvents may be used in combination. In the case where two or more kinds of organic solvents are used in combination, the term "volume concentration of organic solvent" as used herein refers to the sum of the volume concentrations of each organic solvent.

The sulfation reaction solution is preferably a solution containing substantially no organic solvent, more preferably a solution containing no organic solvent. As used herein, the expression "solution containing substantially no organic solvent" refers to a solution containing an organic solvent to such an extent that the resultant sulfated glycosaminoglycan exhibits no or little variation (increased or decrease) in degree of sulfation as compared with the case of use of a solution containing no organic solvent (i.e., a solution prepared by use of an inorganic solvent (e.g., water) in place of an organic solvent mixed for preparation of a solution containing substantially no organic solvent). The expression "little variation in degree of sulfation" may refer to the case where the degree of sulfation or sulfur content of the sulfated glycosaminoglycan varies only by 20% or less, 10% or less, 5% or less, 2% or less, 1% or less, 0.5% or less, or 0.1% or less. That is, the expression "little variation in degree of sulfation" may refer to the case where the degree of sulfation or sulfur content of the sulfated glycosaminoglycan prepared through sulfation reaction by use of a solution containing substantially no organic solvent is 0.8 n % to 1.2 n %, 0.9 n % to 1.1 n %, 0.95 n % to 1.05 n %, 0.98 n % to 1.02 n %, 0.99 n % to 1.01 n %, 0.995 n % to 1.005 n %, or 0.999 n % to 1.001 n % (where n % represents the degree of sulfation or sulfur content of a sulfated glycosaminoglycan prepared through sulfation reaction by use a solution containing no organic solvent). As used herein, the "solution containing substantially no organic solvent" may refer to, for example, a solution containing an organic solvent in an amount (volume concentration (v/v)) of higher than 0% and 20% or lower, higher than 0% and 10% or lower, higher than 0% and 5% or lower, higher than 0% and 2% or lower, higher than 0% and 1% or lower, higher than 0% and 0.5% or lower, or higher than 0% and 0.1% or lower.

No particular limitation is imposed on the amount of the inorganic solvent contained in the sulfation reaction solution, and the amount of the inorganic solvent can be appropriately determined depending on various conditions, such as the type of the inorganic solvent and the desired degree of sulfation. In the sulfation method of the present invention, the inorganic solvent can be used so that, for example, the volume concentration (v/v) of the inorganic solvent contained in the sulfation reaction solution falls within the range described below. The volume concentration of the inorganic solvent may be, for example, 1% or higher, 5% or higher, 10% or higher, 20% or higher, 40% or higher, 60% or higher, 80% or higher, 90% or higher, 95% or higher, 99% or higher, 99.9% or higher, or 100%. The volume concentration of the inorganic solvent may be, for example, 100% or lower, 99% or lower, 95% or lower, 90% or lower, 80% or lower, 60% or lower, 40% or lower, 20% or lower, 10% or lower, or 5% or lower. The volume concentration of the inorganic solvent is preferably, for example, 1% to 100%, 20% to 100%, 40% to 100%, 60% to 100%, 80% to 100%, 90% to 100%, or 95% to 100%. Only one kind of inorganic solvent may be used, or two or more kinds of inorganic solvents may be used in combination. In the case where two or more kinds of inorganic solvents are used in combination, the term "volume concentration of inorganic solvent" as used herein refers to the sum of the volume concentrations of each inorganic solvent.

Example of the strongly basic solution includes a strongly basic solution containing a strong base. No particular limitation is imposed on the strong base, so long as it is a compound which, when coexists with water, provides the solution with strong basicity. The strong base may be a compound which releases a hydroxide ion when coexists with water, or a compound which releases a hydroxide ion when ionized. Thus, the strong base may be an Arrhenius base. No particular limitation is imposed on the type of the strong base. Examples of the strong base include metal hydroxides, tetraalkylammonium hydroxides, guanidine, and ammine complex hydroxides. The strong base is preferably an inexpensive and readily available compound; i.e., a metal hydroxide. Examples of the metal hydroxide include alkali metal hydroxides and alkaline earth metal hydroxides. The metal hydroxide is preferably a compound which is readily discarded or discharged; i.e., an alkali metal hydroxide. Examples of the alkali metal hydroxide include sodium hydroxide, potassium hydroxide, and lithium hydroxide.

No particular limitation is imposed on the amount of the strong base contained in the sulfation reaction solution, and the amount of the strong base can be appropriately determined depending on various conditions, such as the type of the strong base, the desired degree of sulfation, and the pH of the solution. In the sulfation method of the present invention, the strong base can be used so that, for example, the mole concentration of the strong base contained in the sulfation reaction solution falls within the range described below. The mole concentration of the strong base may be, for example, 0.005 M or higher, 0.01 M or higher, 0.05 M or higher, 0.1 M or higher, 0.2 M or higher, 0.5 M or higher, or 1 M or higher. The mole concentration of the strong base may be, for example, 10 M or lower, 5 M or lower, 4 M or lower, or 3 M or lower. The mole concentration of the strong base is preferably, for example, 0.005 M to 10 M, 0.01 M to 5 M, 0.01 M to 4 M, 0.05 M to 5 M, 0.05 M to 4 M, 0.1 M to 5 M, 0.1 M to 4 M, 0.2 M to 5 M, 0.2 M to 4 M, 0.5 M to 5 M, 0.5 M to 4 M, or 1 M to 3 M. Only one kind of strong base may be used, or two or more kinds of strong bases may be used in combination. In the case where two or more kinds of strong bases are used in combination, the term "mole concentration of strong base" as used herein refers to the sum of the mole concentrations of each strong base. The term "mole concentration of strong base" as used herein may refer to the mole concentration of hydroxide ions.

The strong base may be in the form of a gas, a solid (e.g., powder or granule), or a liquid. The "liquid" as used herein may be a gaseous or solid strong base coexistent with a solvent. The "solvent" as used herein may be an organic solvent, an inorganic solvent, or a mixture of an organic solvent and an inorganic solvent. The "solvent" as used herein may be a solvent that dissolves the coexistent strong base, or a solvent that does not dissolve the coexistent strong base. The "solvent that does not dissolve the strong base" as used herein may be a solvent that dissolves no coexistent strong base, or a solvent that partially but not completely dissolves the coexistent strong base.

No particular limitation is imposed on the GAG used for the sulfation method of the present invention, so long as it is recognized as a GAG in the technical field to which the present invention pertains. The GAG is a linear polysaccharide having a backbone structure formed through repeated polymerization of disaccharide units each containing an amino sugar. The amino sugar may be hexosamine (HexN). The amino sugar may be glucosamine (GlcN) or galactosamine (GalN). The hexosamine (HexN) may be N-acetylhexosamine (HexNAc). The hexosamine (HexN) may be N-acetylglucosamine (GlcNAc), or N-acetylgalactosamine (GalNAc).

The GAG used for the sulfation method of the present invention may be a GAG having a sulfate group or a GAG having no sulfate group. Examples of the GAG having a sulfate group include CS, DS, HS, HEP, AS, KS, and KPS. The GAG having a sulfate group may be a GAG sulfated by, for example, the sulfation method of the present invention or a known sulfation method. Examples of the GAG having no sulfate group include CH, HA, HPN, and testosteronan. The GAG used for the sulfation method of the present invention may be a desulfated GAG. The desulfated GAG refers to a GAG having a sulfation degree lower than that of an undesulfated GAG having a sulfate group, and is not limited to a GAG having no sulfate group. No particular limitation is imposed on the GAG used for desulfation reaction, and the GAG may be any of the above-exemplified GAGs having a sulfate group. Examples of the desulfated GAG include dCH, dHEP, and ACH.

The GAG used for the sulfation method of the present invention is preferably a linear polysaccharide having a backbone structure formed through repeated polymerization of disaccharide units each containing an acidic sugar (i.e., an acidic polysaccharide). The acidic sugar may be hexuronic acid (HexA). The acidic sugar may be glucuronic acid (GlcA) or iduronic acid (IdoA). Thus, the GAG used for the sulfation method of the present invention is preferably a GAG having a HexA residue. Examples of the acidic polysaccharide include CS, DS, CH, HA, HS, HEP, HPN, AS, ACH, and testosteronan.

As described above, the GAG used for the sulfation method of the present invention may be a linear polysaccharide having a backbone structure formed through repeated polymerization of disaccharide units each consisting of an amino sugar and an acidic sugar. The GAG used for the sulfation method of the present invention may be a polysaccharide containing an amino sugar and HexA as components. The GAG used for the sulfation method of the present invention may be a polysaccharide containing only an amino sugar and. GlcA as components, a polysaccharide containing only an amino sugar and IdoA as components, or a polysaccharide containing an amino sugar, GlcA, and IdoA as components. Examples of the polysaccharide containing only an amino sugar and GlcA as components include CS, CH, HA, HPN, and testosteronan. Examples of the polysaccharide containing only an amino sugar and IdoA as components include AS and ACH. Examples of the polysaccharide containing an amino sugar, GlcA, and IdoA as components include DS, HS, and HEP.

The polysaccharide containing IdoA as a component may be, besides the above-exemplified polysaccharides, polysaccharide prepared through epimerization of GlcA residues to IdoA residues. For example, the GAG used for the sulfation method of the present invention may be a polysaccharide prepared from the polysaccharide containing GlcA as a component through partial or complete epimerization of GlcA residues to IdoA residues. Examples of such a polysaccharide include isomers of HPN (epimerized heparosan) prepared through partial or complete epimerization of GlcA residues to IdoA residues. The epimerization of HPN can be performed by, for example, the method described in the document (WO 2014/200045).

The polysaccharide containing GlcA as a component may be, besides the above-exemplified polysaccharides, a polysaccharide prepared through epimerization of IdoA residues to GlcA residues. For example, the GAG used for the sulfation method of the present invention may be a polysaccharide prepared from the polysaccharide containing IdoA as a component through partial or complete epimerization of IdoA residues to GlcA residues. Examples of such a polysaccharide include isomers of dHEP or HEP (epimerized heparin), and isomers of ACH and AS (epimerized acharan) prepared through partial or complete epimerization of IdoA residues to GlcA residues. The epimerization of dHEP or ACH can be performed by, for example, the method described in the document (WO 2014/200045).

The GAG used for the sulfation method of the present invention may be a GAG having a branched sugar residue or a GAG having no branched sugar residue. Examples of the branched sugar residue include a fructose (Frc) residue. Examples of the GAG having a branched sugar residue include K4 polysaccharide (fructosylated chondroitin), which is CH having a branched sugar residue of Frc. The GAG used for the sulfation method of the present invention is preferably a GAG having no branched sugar residue.

The GAG used for the sulfation method of the present invention may be the GAG itself or a GAG derivative. The term "GAG derivative" refers to a derivative prepared through addition or elimination of a substituent or a functional group to or from a GAG. No particular limitation is imposed on the GAG derivative, so long as it has a moiety to be sulfated by the sulfation method of the present invention. Examples of the moiety to be sulfated by the sulfation method of the present invention include a hydroxy group and an amino group. The "hydroxy group" as used herein may be a hydroxy group inherent in a GAG (i.e., a hydroxy group on a sugar residue of the GAG). The "amino group" as used herein may be an amino group inherent in a GAG (i.e., an amino group on a sugar residue of the GAG). Examples of the GAG derivative include a GAG prepared through elimination of an acetyl group (deacetylated GAG) and a GAG prepared through addition of a hydrophobic group (e.g., an alkyl group such as a methyl group, an acyl group such as an acetyl group, or an aryl group such as a phenyl group).

The GAG derivative used for the sulfation method of the present invention may be a GAG prepared through elimination of an acetyl group (i.e., deacetylation) (hereinafter the GAG referred to as "deacetylated GAG"). The term "deacetylation" as used herein may be deacetylation of an amino group (N-deacetylation). In one embodiment, the deacetylated GAG may be an N-deacetylated GAG. The deacetylated GAG may be prepared through complete or partial elimination of an acetyl group from a sugar residue of a GAG. The GAG derivative used for the sulfation method of the present invention may be a GAG prepared through introduction of an alkyl group (alkylation) (hereinafter the GAG referred to as "alkylated GAG"). The term "alkylation" as used herein may be alkylation of a hydroxy group (O-alkylation). In one embodiment, the alkylated GAG may be an O-alkylated GAG. The alkylated GAG may be prepared through complete or partial alkylation of a functional group (e.g., a primary or secondary hydroxy group, or an aldehyde group) of a sugar residue of a GAG. Examples of the alkylation include methylation and ethylation.

No particular limitation is imposed on the origin of the GAG used for the sulfation method of the present invention. The sulfation method of the present invention may involve the use of, for example, a chemically synthesized GAG, an enzymatically synthesized. GAG, or a GAG derived from an animal or a microorganism. The GAG used for the sulfation method of the present invention may be prepared by, for example, any known method, or may be a commercially available product.

The GAG used for the sulfation method of the present invention may be the GAG itself or may be in the form of a complex with an additional substance. No particular limitation is imposed on the additional substance, and example of the additional substance includes a protein. In the sulfation method of the present invention, a complex of a GAG with a protein (e.g., proteoglycan) may be used for the sulfation reaction of GAG. Preferably, the GAG used for the sulfation method of the present invention is not in the form of a complex with an addition substance.

No particular limitation is imposed on the molecular weight of the GAG used for the sulfation method of the present invention, and the molecular weight may be any value. The molecular weight may be, for example, 4 MDa (megadalton) (4,000,000 Da) or lower, 3 MDa or lower, 2 MDa or lower, 1 MDa or lower, 500 kDa or lower, 200 kDa or lower, 100 kDa or lower, or 50 kDa or lower. The molecular weight may be, for example, 5 kDa or higher, 10 kDa or higher, 20 kDa or higher, 30 kDa or higher, 50 kDa or higher, 100 kDa or higher, 500 kDa or higher, 1 MDa or higher, or 2 MDa or higher. The molecular weight is preferably, for example, 5 kDa to 4 MDa, 5 kDa to 3 MDa, 5 kDa to 2 MDa, 5 kDa to 1 MDa, 5 kDa to 500 kDa, 5 kDa to 100 kDa, 5 kDa to 50 kDa, 10 kDa to 3 MDa, 10 kDa to 1 MDa, 10 kDa to 500 kDa, 10 kDa to 100 kDa, 10 kDa to 50 kDa, 20 kDa to 100 kDa, 20 kDa to 50 kDa, 30 kDa to 50 kDa, 500 kDa to 4 MDa, 500 kDa to 3 MDa, 1 MDa to 4 MDa, 1 MDa to 3 MDa, or 2 MDa to 3 MDa. The term "molecular weight" as used herein refers to a weight average molecular weight. In the case where the GAG is in the form of a complex with an additional substance, the molecular weight may be that of the GAG itself. The molecular weight of the GAG can be measured by, for example, any known method. Specifically, the molecular weight of the GAG may be a weight average molecular weight measured by means of, for example, size exclusion chromatography. More specifically, the molecular weight of the GAG can be measured by, for example, the method described in <Referential Example 4> or <Referential Example 5> hereinbelow.

No particular limitation is imposed on the amount of the GAG contained in the sulfation reaction solution, and the amount of the GAG can be appropriately determined depending on various conditions, such as the type and volume of the strongly basic solution and the desired degree of sulfation. In the sulfation method of the present invention, the GAG can be used so that, for example, the weight concentration (w/v) of the GAG contained in the sulfation reaction solution falls within the range described below. The weight concentration of the GAG may be, for example, 0.001% or higher, 0.01% or higher, 0.1% or higher, or 1% or higher. The weight concentration of the GAG may be, for example, 50% or lower, 40% or lower, 30% or lower, or 20% or lower. The weight concentration of the GAG is preferably, for example, 0.001% to 50%, 0.01% to 40%, 0.1% to 30%, 0.1% to 20%, 1% to 20%, 1% to 10%, 0.1% to 10%, or 0.1% to 1%, Only one kind of GAG may be used, or two or more kinds of GAGs may be used in combination. In the case where two or more kinds of GAGs are used in combination, the term "weight concentration of GAG" as used herein refers to the sum of the weight concentrations of each GAG. The term "weight concentration of GAG" as used herein may be a value obtained by dividing the weight of dry powder of GAG by the amount of the sulfation reaction solution, or may be determined by an analytical method for GAG concentration. The analytical method for GAG concentration is, for example, the carbazole sulfate method (BITTER T, MUIR H M., Anal. Biochem, 1962 October; 4: 330-4).

The GAG may be in the form of a solid (e.g., a vacuum-dried, lyophilized, powdery, or granular product) or in the form of a liquid. The "liquid" as used herein may be a solid GAG coexistent with a solvent. The "solvent" as used herein may be an organic solvent, an inorganic solvent, or a mixture of an organic solvent and an inorganic solvent. The "solvent" as used herein may be a solvent that dissolves the coexistent GAG, or a solvent that does not dissolve the coexistent GAG. The "solvent that does not dissolve the GAG" as used herein may be a solvent that dissolves no coexistent GAG, or a solvent that partially but not completely dissolves the GAG.

No particular limitation is imposed on the sulfating agent, so long as it is a compound capable of sulfating a GAG. The sulfating agent may be, for example, any known sulfating agent that is generally used for sulfation reaction. The sulfating agent may be, for example, sulfur trioxide itself, a sulfur trioxide composition, or a halogenated sulfonic acid (e.g., chlorosulfonic acid). The sulfating agent is preferably a sulfur trioxide composition. Example of the sulfur trioxide composition includes a sulfur trioxide complex. The sulfur trioxide complex is a compound prepared through coordinate bonding of sulfur trioxide and a Lewis base. Examples of the "Lewis base" as used herein include an amine or pyridine. Examples of the sulfur trioxide complex include a complex composed of sulfur trioxide and an amine (sulfur trioxide-amine complex) and a complex composed of sulfur trioxide and pyridine (sulfur trioxide-pyridine complex). Examples of the sulfur trioxide-amine complex include a sulfur trioxide-trialkylamine complex. Examples of the sulfur trioxide-trialkylamine complex include a sulfur trioxide-trimethylamine complex, a sulfur trioxide-dimethylethylamine complex, a sulfur trioxide-methyldiethylamine complex, and a sulfur trioxide-triethylamine complex.

No particular limitation is imposed on the amount of the sulfating agent contained in the sulfation reaction solution, and the amount of the sulfating agent can be appropriately determined depending on various conditions, such as the type of the sulfating agent and the desired degree of sulfation. In the sulfation method of the present invention, the sulfating agent can be used so that, for example, the weight concentration (w/v) of the sulfating agent contained in the sulfation reaction solution falls within the range described below. The weight concentration of the sulfating agent may be, for example, 0.001% or higher, 0.01% or higher, 0.1% or higher, or 1% or higher. The weight concentration of the sulfating agent may be, for example, 100% or lower, 60% or lower, 40% or lower, or 20% or lower. The weight concentration of the sulfating agent is preferably, for example, 0.001% to 100%, 0.01% to 60%, 0.1% to 40%, or 1% to 20%, Only one kind of sulfating agent may be used, or two or more kinds of sulfating agents may be used in combination, in the case where two or more kinds of sulfating agents are used in combination, the term "weight concentration of sulfating agent" as used herein refers to the sum of the weight concentrations of each sulfating agent.

In the sulfation method of the present invention, the sulfating agent can be used so that, for example, the amount of the sulfating agent relative to the total number of disaccharide units of the GAG contained in the sulfation reaction solution falls within the equivalent range described below. Unless otherwise specified, the "equivalent" in terms of the amount of the sulfating agent described below refers to the "mole equivalent." The amount of the sulfating agent relative to the total number of disaccharide units of the GAG may be, for example, 0.001 equivalents or higher, 0.01 equivalents or higher, or 0.1 equivalents or higher. The amount of the sulfating agent relative to the total number of disaccharide units of the GAG may be, for example, 200 equivalents or lower, 120 equivalents or lower, 60 equivalents or lower, 30 equivalents or lower, 10 equivalents or lower, or 5 equivalents or lower. The amount of the sulfating agent relative to the total number of disaccharide units of the GAG is preferably, for example, 0.001 equivalents to 200 equivalents, 0.01 equivalents to 120 equivalents, 0.1 equivalents to 60 equivalents, 0.1 equivalents to 30 equivalents, 0.1 equivalents to 10 equivalents, or 0.1 equivalents to 5 equivalents. In the case where two or more kinds of sulfating agents are used in combination, the "amount of the sulfating agent relative to the total number of disaccharide units of the GAG" as used herein refers to the sum of the amounts of each sulfating agent relative to the total number of disaccharide units of the GAG. The total number of disaccharide units of the GAG can be measured by, for example, any known method. Specifically, the total number of disaccharide units of the GAG can be measured by, for example, the disaccharide analysis method described in <Referential Example 6>, <Referential Example 10>, or <Referential Example 11> hereinbelow. Alternatively, the total number of disaccharide units of the GAG can be measured by, for example, the carbazole sulfate method (BITTER T, MUIR H M., Anal. Biochem. 1962 October; 4: 330-4).

The sulfating agent may be in the form of a gas, a solid (e.g., powder or granule), or a liquid. The "liquid" as used herein may be a gaseous or solid sulfating agent coexistent with a solvent. The "solvent" as used herein may be an organic solvent, an inorganic solvent, or a mixture of an organic solvent and an inorganic solvent. The "solvent" as used herein may be a solvent that dissolves the coexistent sulfating agent, or a solvent that does not dissolve the coexistent sulfating agent. The "solvent that does not dissolve the sulfating agent" as used herein may be a solvent that dissolves no coexistent sulfating agent, or a solvent that partially but not completely dissolves the coexistent sulfating agent.

The sulfation reaction solution may be a strongly basic solution containing only a GAG and a sulfating agent as other components except a solvent; a strongly basic solution containing only a GAG, a sulfating agent, and a strong base as other components except, a solvent; or a strongly basic solution containing an additional component besides these components except a solvent. No particular limitation is imposed on the "additional component" as used herein, so long as the sulfation reaction can be performed even in the presence of the additional component in the sulfation reaction solution. Examples of the additional component include an alkali metal salt, an alkaline earth metal salt, a phosphate salt, a sulfate salt, a surfactant, a buffer, and a component derived from an animal or microorganism from which the GAG is extracted (e.g., a nucleic acid, a protein, a carbohydrate, or a lipid). Specific examples of the additional component include sodium sulfate, and a component derived from a microorganism (e.g., *Escherichia coli*).

In the sulfation method of the present invention, the materials used for the sulfation reaction may be sequentially added in any order or may be simultaneously added so that the materials coexist together. For example, the sulfation reaction may be performed through addition, in any order, of a GAG, a sulfating agent, and an inorganic solvent, and optionally a strong base, an additional component, and an organic solvent. In the sulfation method of the present invention, an optional solvent may further be added after the preparation of the sulfation reaction solution. In the case where, for example, the strong base or the sulfating agent is not dissolved partially or completely in the prepared sulfation reaction solution, a solvent required for dissolution of the strong base or the sulfating agent can further be added to the solution for complete dissolution thereof. For the preparation of the sulfation reaction solution, appropriate agitation and mixing are preferably performed after addition of each of the materials used.

In the sulfation method of the present invention, the GAG may be undissolved in the sulfation reaction solution, may be partially but not completely dissolved in the solution, or may be completely dissolved in the solution. In the case where the GAG is undissolved in the sulfation reaction solution or is partially but not completely dissolved in the solution, preferably, the GAG is dispersed in the solvent through appropriate agitation of the sulfation reaction solution.

No particular limitation is imposed on the sulfation reaction temperature, and the sulfation reaction temperature can be appropriately determined depending on various conditions, such as the type of the sulfating agent and the desired degree of sulfation. In the sulfation method of the present invention, the sulfation reaction temperature can be determined so as to fall within, for example, the temperature range described below. The sulfation reaction temperature may be, for example, 0° C. or higher, 4° C. or higher, 10° C. or higher, 20° C. or higher, 30° C. or higher, or 40° C. or higher. The sulfation reaction temperature may be, for example, 100° C. or lower, 90° C. or lower, 80° C. or lower, 70° C. or lower, or 60° C. or lower. The sulfation reaction temperature is preferably, for example, 0° C. to 100° C., 0° C. to 60° C., 4° C. to 90° C., 4° C. to 60° C., 10° C. to 80° C., 20° C. to 70° C., 20° C. to 60° C., 30° C. to 70° C., or 40° C. to 60° C.

No particular limitation is imposed on the sulfation reaction time, and the sulfation reaction time can be appropriately determined depending on various conditions, such as the type of the sulfating agent and the desired degree of sulfation. In the sulfation method of the present invention, the sulfation reaction time can be determined so as to fall within, for example, the time range described below. The sulfation reaction time may be, for example, 1 minute or longer, 5 minutes or longer, 10 minutes or longer, 20 minutes or longer, 30 minutes or longer, or 1 hour or longer. The sulfation reaction time may be, for example, 168 hours or shorter, 48 hours or shorter, 24 hours or shorter, 18 hours or shorter, 6 hours or shorter, or 3 hours or shorter. The sulfation reaction time is preferably, for example, 1 minute to 168 hours, 5 minutes to 168 hours, 5 minutes to 48 hours, 10 minutes to 24 hours, 20 minutes to 18 hours, 30 minutes to 6 hours, or 1 hour to 3 hours.

The sulfation reaction may be performed while the sulfation reaction solution is allowed to stand still. Preferably, the sulfation reaction solution is appropriately agitated so that the GAG and the sulfating agent are uniformly dispersed in the solution.

In the present invention, the sugar residue (e.g., HexN or HexA) is preferably a D-form.

The sulfation method of the present invention can sulfate a GAG. In the sulfation method of the present invention, the sulfation may be sulfation of an amino group (N-sulfation) and/or sulfation of a hydroxy group (O-sulfation). In other words, the sulfation may be N-sulfation and O-sulfation (N,O-sulfation), N-sulfation, or O-sulfation.

(2) Production Method 1 for Sulfated GAG of the Present Invention

The production method 1 for sulfated GAG of the present invention (hereinafter referred to as "the production method 1 of the present invention") is characterized by comprising a step of performing the sulfation method of the present invention.

As used herein, the term "sulfated GAG" refers to a GAG exhibiting a degree of sulfation higher than that of the GAG before the sulfation reaction; i.e., a GAG exhibiting an index indicating the degree of sulfation higher than that of the GAG before the sulfation reaction.

The index indicating the degree of sulfation of a GAG can be represented by, for example, the percentage of a value calculated by dividing the number of sulfate groups of the GAG by the number of disaccharide units (i.e., the average number of sulfate groups per disaccharide unit) (hereinafter the percentage referred to as "sulfation degree"). The sulfation degree can be calculated by, for example, any known technique. Specifically, the sulfation degree can be calculated by, for example, the method described in <Referential Example 7>, <Referential Example 8>, or <Referential Example 13>.

The index indicating the degree of sulfation of a GAG can also be represented by, for example, the percentage of a value calculated by dividing the amount of atomic sulfur contained in the GAG (i.e., a value obtained through multiplication of the number of sulfur atoms of the GAG by the atomic weight of sulfur) by the molecular weight of the GAG (i.e., the weight percent concentration (w/w) of the total weight of sulfur atoms relative to the total weight of atoms constituting the GAG) (hereinafter the percentage referred to as "sulfur content"). The sulfur content can be measured by, for example, any known technique. Specifically, the sulfur content can be measured by, for example, the oxygen flask combustion method. Alternatively, the sulfur content can be calculated by, for example, the method described in <Referential Example 9> or <Referential Example 12>.

As described above, the GAG used for the sulfation method of the present invention may be a GAG itself, an epimerized GAG, a GAG having a branched sugar residue, or a GAG derivative. Thus, in the present invention, the sulfated GAG may be prepared by sulfation of a GAG itself, sulfation of an epimerized GAG, sulfation of a GAG having a branched sugar residue, or sulfation of a GAG derivative. Examples of the GAG derivative include a deacetylated GAG and a GAG prepared through addition of a hydrophobic group (e.g., an alkyl group such as a methyl group, an acyl group such as an acetyl group, or an aryl group such as a phenyl group). Specific examples of the GAG derivative include a deacetylated GAG and an alkylated GAG. In the present invention, the sulfated GAG may be a sulfated GAG derivative. Specific examples of the sulfated GAG derivative include a sulfated deacetylated GAG or a sulfated alkylated GAG.

The production method 1 of the present invention, besides comprising a step of performing the sulfation method of the present invention, may optionally further comprise an additional step. The "additional step" as used herein is for example, a step of terminating the sulfation reaction. The sulfation reaction can be terminated by adjusting the pH of the sulfation reaction solution to a level lower than the pH suitable for the sulfation reaction, preferably by adjusting the pH of the sulfation reaction solution to a pH within a neutral or weakly acidic range. Specifically, the sulfation reaction can be terminated by, for example, adjusting the pH of the sulfation reaction solution to 0 to 8, preferably 2 to 8, more preferably 4 to 8, still more preferably 6 to 8. The sulfation reaction can be terminated by, for example, adding a neutralizing component or an acidic component to the sulfation reaction solution. No particular limitation is imposed on the "acidic component" as used herein, so long as it is a compound that acidifies the solution when coexists with water. Specific examples of the acidic component include acetic acid and hydrochloric acid.

The "additional step" as used herein is, for example, a step of acetylating the sulfated GAG. No particular limitation is imposed on the method for acetylating the sulfated GAG, and the acetylation may be performed by, for example, any known method. The method for acetylating the sulfated GAG is, for example, a method involving the use of acetic anhydride. The method involving the use of acetic anhydride is described in, for example, the known document (Purkerson M L, Tollefsen D M, Klahr S., J. Clin. Invest. 1988 January; 81(1): 69-74).

The "additional step" as used herein is, for example, a step of purifying the sulfated GAG. No particular limitation is imposed on the method for purifying the sulfated GAG, and the purification may be performed by, for example, any known method Examples of the method for purifying the sulfated GAG include the alcohol precipitation method utilizing a solvent (e.g., ethanol), and chromatography (e.g., anion-exchange chromatography).

(3) Production Method 2 for Sulfated GAG of the Present Invention

The production method 2 for sulfated GAG of the present invention (hereinafter referred to as "the production method 2 of the present invention") is a method for producing a sulfated GAG characterized by, besides comprising a step of performing the sulfation reaction by the sulfation method of the present invention, comprising a step of performing deacetylation reaction of the GAG (reaction to deacetylate the GAG). The sulfated GAG produced by the production method 2 of the present invention is a GAG exhibiting a degree of acetylation lower than that of the GAG before the sulfation reaction and the deacetylation reaction; i.e., a GAG exhibiting an index indicating the degree of acetylation lower than that of the GAG before the sulfation reaction and the deacetylation reaction. The index indicating the degree of acetylation can be represented by, for example, the percentage of a value calculated by dividing the number of acetyl groups of the GAG by the number of disaccharide units (i.e., the average number of acetyl groups per disaccharide unit) (hereinafter the percentage referred to as "deacetylation degree").

In the production method 2 of the present invention, the deacetylation may be deacetylation of an amino group (N-deacetylation) and/or deacetylation of a hydroxy group (O-deacetylation). In other words, the deacetylation may be N-deacetylation and O-deacetylation (N,O-deacetylation), N-deacetylation, or O-deacetylation. The term "amino group" as used herein may be an amino group inherent in a GAG (i.e., an amino group on a sugar residue of the GAG). The term "hydroxy group" as used herein may be a hydroxy group inherent in a GAG (i.e., a hydroxy group on a sugar residue of the GAG).

In the production method 2 of the present invention, the deacetylation reaction is performed by, for example, alkaline hydrolysis. In the production method 2 of the present invention, the deacetylation reaction can be performed, for example, under coexistence of a basic solution with the GAG. Thus, the deacetylation reaction can be performed through, for example, addition of the GAG to a basic solution, or basification of a solution containing the GAG.

In the production method 2 of the present invention, the deacetylation reaction and the sulfation reaction may be performed simultaneously; the deacetylation reaction may be followed by the sulfation reaction; or the sulfation reaction may be followed by the deacetylation reaction. In the production method 2 of the present invention, the pH of the solution and the components contained in the solution during the deacetylation reaction may be the same as or different from those during the sulfation reaction. For example, in the case where the deacetylation reaction is followed by the sulfation reaction, the pH of the solution may be varied through addition of an acid or a base after the deacetylation reaction, followed by the sulfation reaction, or the components contained in the solution may be varied through addition of another component after the deacetylation reaction, followed by the sulfation reaction.

No particular limitation is imposed on the pH of the solution during the deacetylation reaction (hereinafter referred to as "pH during the deacetylation reaction"), and the pH can be appropriately determined depending on various conditions, such as the desired degree of deacetylation. The pH during the deacetylation reaction may be, for example, 11 or higher, 11.5 or higher, 12 or higher, 12.5 or higher, or 13 or higher. The pH during the deacetylation reaction may be, for example, 14 or lower or 13.5 or lower.

No particular limitation is imposed on the temperature of the solution during the deacetylation reaction (hereinafter referred to as "temperature during the deacetylation reaction"), and the temperature can be appropriately determined depending on various conditions, such as the pH of the solution and the desired degree of deacetylation. The temperature during the deacetylation reaction can be determined so as to fall within, for example, the temperature range described below. The temperature during the deacetylation reaction may be, for example, 20° C. or higher, 30° C. or higher, or 40° C. or higher. The temperature during the deacetylation reaction may be, for example, 100° C. or lower, 90° C. or lower, 80° C. or lower, 70° C. or lower, or 60° C. or lower. The temperature during the deacetylation reaction is preferably, for example, 20° C. to 100° C., 20° C. to 90° C., 30° C. to 80° C., 30° C. to 70° C., or 40° C. to 60° C.

No particular limitation is imposed on the deacetylation reaction time, and the deacetylation reaction time can be appropriately determined depending on various conditions, such as the temperature or the pH of the solution and the desired degree of deacetylation. The deacetylation reaction time can be determined so as to fall within, for example, the time range described below. The deacetylation reaction time may be, for example, 1 minute or longer, 5 minutes or longer, 10 minutes or longer, 30 minutes or longer, or 1 hour or longer. The deacetylation reaction time may be, for example, 72 hours or shorter, 48 hours or shorter, 24 hours or shorter, 8 hours or shorter, or 4 hours or shorter. The deacetylation reaction time is preferably, for example, 1 minute to 72 hours, 5 minutes to 48 hours, 10 minutes to 24 hours, 30 minutes to 8 hours, or 1 hour to 4 hours.

The production method 2 of the present invention may optionally further comprise an additional step. Examples of the "additional step" as used herein include the additional steps described above in the production method 1 of the present invention.

(4) Production Method 3 for Sulfated GAG of the Present Invention

The production method 3 for sulfated GAG of the present invention (hereinafter referred to as "the production method 3 of the present invention") is the method for producing a sulfated GAG characterized by, besides comprising a step of perform the sulfation reaction by the sulfation method of the present invention, comprising a step of performing alkylation reaction of the GAG (reaction to alkylate the GAG). The sulfated GAG produced by the production method 3 of the present invention is a GAG exhibiting a degree of alkylation higher than that of the GAG before the sulfation reaction and the alkylation reaction; i.e., a GAG exhibiting an index indicating the degree of alkylation higher than that of the GAG before the sulfation reaction and the alkylation reaction. The index indicating the degree of alkylation can be represented by, for example, the percentage of a value calculated by dividing the number of alkyl groups of the GAG by the number of disaccharide units (i.e., the average number of alkyl groups per disaccharide unit) (hereinafter the percentage referred to as "alkylation degree"). Specific examples of the "alkylation" as used herein include methylation or ethylation.

In the production method 3 of the present invention, the alkylation may be alkylation of an amino group (N-alkylation) and/or alkylation of a hydroxy group (O-alkylation). In other words, the alkylation may be N-alkylation and O-alkylation (N,O-alkylation), N-alkylation, or O-alkylation. The term "amino group" as used herein may be an amino group inherent in a GAG (i.e., an amino group on a sugar residue of the GAG). The term "hydroxy group" as used herein may be a hydroxy group inherent in a GAG (i.e., a hydroxy group on a sugar residue of the GAG).

In the production method 3 of the present invention, the alkylation reaction may be performed under coexistence of the GAG with an alkylating agent in a basic solution. Thus, the alkylation reaction can be performed through, for example, addition of an alkylating agent to a basic solution containing the GAG, addition of the GAG to a basic solution containing an alkylating agent, or basification of a solution containing the GAG and an alkylating agent.

The alkylating agent may be any known alkylating agent that is generally used for alkylation reaction. No particular limitation is imposed on the alkylating agent, so long as it is a compound capable of alkylating the GAG. Examples of the alkylating agent include an alkyl halide. Examples of the alkyl halide include iodomethane and iodoethane.

In the production method 3 of the present invention, the alkylation reaction and the sulfation reaction may be performed simultaneously; the alkylation reaction may be followed by the sulfation reaction; or the sulfation reaction may be followed by the alkylation reaction. In the production method 3 of the present invention, the pH of the solution and the components contained in the solution during the alkylation reaction may be the same as or different from those during the sulfation reaction. For example, in the case where the alkylation reaction is followed by the sulfation reaction, the pH of the solution may be varied through addition of an acid or a base after the alkylation reaction, followed by the sulfation reaction, or the components contained in the solution may be varied through addition of another component after the alkylation reaction, followed by the sulfation reaction.

No particular limitation is imposed on the pH of the solution during the alkylation reaction (hereinafter referred to as "pH during the alkylation reaction"), and the pH can be appropriately determined depending on various conditions, such as the desired degree of alkylation. The pH during the alkylation reaction may be, for example, 11 or higher, 11.5 or higher, 12 or higher, 12.5 or higher, or 13 or higher. The pH during the alkylation reaction may be, for example, 14 or lower or 13.5 or lower.

No particular limitation is imposed on the temperature of the solution during the alkylation reaction (hereinafter referred to as "temperature during the alkylation reaction"), and the temperature can be appropriately determined depending on various conditions, such as the pH of the solution and the desired degree of alkylation. The temperature during the alkylation reaction can be determined so as to fall within, for example, the temperature range described below. The temperature during the alkylation reaction may be, for example, 20° C. or higher, 30° C. or higher, or 40° C. or higher. The temperature during the alkylation reaction may be, for example, 100° C. or lower, 90° C. or lower, 80° C. or lower, 70° C. or lower, or 60° C. or lower. The temperature during the alkylation reaction is preferably, for example, 20° C. to 100° C., 20° C. to 90° C., 30° C. to 80° C., 30° C. to 70° C., or 40° C. to 60° C.

No particular limitation is imposed on the alkylation reaction time, and the alkylation reaction time can be appropriately determined depending on various conditions, such as the temperature or the pH of the solution and the desired degree of alkylation. The alkylation reaction time can be determined so as to fall within, for example, the time range described below. The alkylation reaction time may be, for example, 1 minute or longer, 5 minutes or longer, 10 minutes longer, 30 minutes or longer, or 1 hour or longer. The alkylation reaction time may be, for example, 72 hours or shorter, 48 hours or shorter, 24 hours or shorter, 8 hours or shorter, or 4 hours or shorter. The alkylation reaction time is preferably, for example, 1 minute to 72 hours, 5 minutes to 48 hours, 10 minutes to 24 hours, 30 minutes to 8 hours, or 1 hour to 4 hours.

The production method 3 of the present invention may optionally further comprise an additional step. Examples of the "additional step" as used herein include the additional steps described above in the production method 1 of the present invention.

The description of the strongly basic solution in the production method 1 of the present invention may be applied to the basic solution used in the production methods 2 and 3 of the present invention. For example, the basic solution may contain a strong base. In such a case, the description about the strong base in the production method 1 of the present invention is applied, mutatis mutandis, to the strong base contained in the basic solution.

In one embodiment, each of the production methods 1, 2, and 3 of the present invention (hereinafter collectively referred to as "the production method of the present invention") may be a method for producing a GAG in which both an amino group and a hydroxy group are sulfated (N,O-sulfated GAG), a method for producing a GAG in which an amino group is sulfated (N-sulfated GAG), or a method for producing a GAG in which a hydroxy group is sulfated (O-sulfated GAG). In the case where the production method of the present invention is characterized by including two or more reactions, the production method may be characterized in that these reactions are performed through one-pot procedure. For example, the production method 2 of the present invention may be characterized in that the sulfation reaction and the deacetylation reaction are performed through one-pot procedure. For example, the production method 3 of the present invention may be characterized in that the sulfation reaction and the alkylation reaction are performed through one-pot procedure. The term "one-pot procedure" refers to a method for synthesizing a target product, in case that multistep synthesis process involving two or more reactions is performed, without purification nor isolation of a reaction intermediate. In the production method of the present invention, the one-pot procedure may be a method for synthesizing a target product further without replacement of a solvent.

(5) Sulfated GAG of the Present Invention

No particular limitation is imposed on the composition ratio of disaccharide units (hereinafter referred to as "disaccharide composition ratio") of a sulfated GAG produced by the production method of the present invention (hereinafter referred to as "the sulfated GAG of the present invention"). The disaccharide composition ratio of the sulfated GAG of the present invention can be adjusted to any value depending on various conditions for the sulfation method of the present invention. Specifically, the sulfated GAG (i.e., reaction product) exhibiting desired disaccharide composition ratio can be produced by appropriately determining various conditions, including the type and concentration of the GAG, the type and amount of a sulfating agent or a strong base, pH, reaction time, reaction temperature, and the concentration of an organic solvent.

The sulfated GAG of the present invention may be characterized by, for example, the disaccharide composition ratio as described below.

Unless otherwise specified, the symbol "%" in terms of the disaccharide composition ratio described below refers to "mol %." In the sulfated GAG of the present invention, the disaccharide composition ratio may be any value. The sulfated GAG of the present invention may be characterized by, for example, the disaccharide composition ratio as described below. In the sulfated GAG of the present invention, each disaccharide may exhibit a disaccharide composition ratio of, for example, 99.9% or lower, 99% or lower, 95% or lower, 90% or lower, 85% or lower, 80% or lower, 75% or lower, 70% or lower, 65% or lower, 60% or lower, 55% or lower, 50% or lower, 45% or lower, 40% or lower, 35% or lower, 30% or lower, 25% or lower, 20% or lower, 15% or lower, 10% or lower, 9% or lower, 8% or lower, 7% or lower, 6% or lower, 5% or lower, 4% or lower, 3% or lower, 2% or lower, or 1% or lower. In the sulfated GAG of the present invention, each disaccharide may exhibit a disaccharide composition ratio of, for example, 0.001% or higher, 0.01% or higher, 0.1% or higher, 1% or higher, 2% or higher, 3% or higher, 4% or higher, 5% or higher, 6% or higher, 7% or higher, 8% or higher, 9% or higher, 10% or higher, 20% or higher, 30% or higher, 40% or higher, 50% or higher, 60% or higher, 70% or higher, 80% or higher, or 90% or higher. In the sulfated GAG of the present invention, each disaccharide preferably exhibits a disaccharide composition ratio of, for example, 0.1% to 99.9%, 0.1% to 99%, 0.1% to 95%, 0.1% to 90%, 0.1% to 85%, 0.1% to 80%, 0.1% to 75%, 0.1% to 70%, 0.1% to 65%, 0.1% to 60%, 0.1% to 55%, 0.1% to 50%, 0.1% to 45%, 0.1% to 40%, 0.1% to 35%, 0.1% to 30%, 0.1% to 25%, 0.1% to 20%, 0.1% to 15%, 0.1% to 10%, 0.1% to 9%, 0.1% to 8%, 0.1% to 7%, 0.1% to 6%, 0.1% to 5%, 0.1% to 4%, 0.1% to 3%, 0.1% to 2%, 0.1% to 1%, 1% to 5%, 1% to 6%, 1% to 7%, 1% to 8%, 1% to 9%, 1% to 10%, 1% to 15%, 1% to 20%, 1% to 25%, 2% to 5%, 2% to 6%, 2% to 7%, 2% to 8%, 2% to 9%, 2% to 10%, 2% to 15%, 2% to 20%, 2% to 25%, 3% to 5%, 3% to 6%, 3% to 7%, 3% to 8%, 3% to 9%, 3% to 10%, 3% to 15%, 3% to 20%, 3% to 25%, 4% to 5%, 4% to 6%, 4% to 7%, 4% to 8%, 4% to 9%, 4% to 10%, 4% to 15%, 4% to 20%, 4% to 25%, 5% to 6%, 5% to 7%, 5% to 8%, 5% to 9%, 5% to 10%, 5% to 15%, 5% to 20%, 5% to 25%, 5% to 30%, 5% to 40%, 5% to 50%, 5% to 60%, 5% to 70%, 5% to 80%, 5% to 90%, 10% to 15%, 10% to 20%, 10% to 25%, 10% to 30%, 10% to 40%, 10% to 50%, 10% to 60%, 10% to 70%, 10% to 80%, 10% to 90%, 15% to 20%, 15% to 25%, 15% to 30%, 15% to 40%, 15% to 50%, 15% to 60%, 15% to 70%, 15% to 80%, 15% to 90%, 20% to 25%, 20% to 30%, 20% to 40%, 20% to 50%, 20% to 60%, 20% to 70%, 20% to 80%, 20% to 90%, 25% to 30%, 25% to 40%, 25% to 50%, 25% to 60%, 25% to 70%, 25% to 80%, 25% to 90%, 30% to 40%, 30% to 50%, 30% to 60%, 30% to 70%, 30% to 80%, 30% to 90%, 40% to 50%, 40% to 60%, 40% to 70%, 40% to 80%, or 40% to 90%.

The disaccharide composition ratio of the sulfated GAG of the present invention can be determined by, for example, any known method. Specifically, the disaccharide composition ratio can be determined by, for example, the disaccharide analysis method described in <Referential Example 6>, <Referential Example 10>, or <Referential Example 1> hereinbelow.

(6) Sulfated Chondroitin of the Present Invention (Chondroitin Sulfate of the Present Invention)

In the case where the sulfated GAG of the present invention is a GAG prepared through sulfation of CH (hereinafter referred to as "sulfated CH of the present invention"), the sulfated GAG may be characterized by, for example, the disaccharide composition ratio as described below. In the following description, a disaccharide containing a structure represented by [HexA1-3GalN1-4] is abbreviated as "CH-0S"; a disaccharide containing a structure represented by [HexA1-3GalN(6S)1-4] is abbreviated as "CH-6S"; a disaccharide containing a structure represented by [HexA-3GalN(4S)1-4] is abbreviated as "CH-4S"; disaccharide containing a structure represented by [HexA(2S)1-3GalN1-4] is abbreviated as "CH-2S"; a disaccharide containing a structure represented by [HexA(2S)1-3GalN(6S)1-4] is abbreviated as "CH-diS$_D$"; a disaccharide containing a structure represented by [HexA1-3GalN(4,6S)1-4] is abbreviated as "CH-diS$_E$"; a disaccharide containing a structure represented by [HexA(2S)1-3GalN(4S)1-4] is abbreviated as "CH-diS$_3$"; and a disaccharide containing a structure represented by [HexA(2S)1-3GalN(4,6S)1-4] is abbreviated as "CH-triS." In the aforementioned formulae, "1-3" represents a 1-3 glycosidic bond; "1-4" represents a 1-4 glycosidic bond; "6S" represents a 6-O-sulfate group; "4S" represents a 4-O-sulfate group; and "2S" represents a 2-O-sulfate group, "HexA" may be GlcA or IdoA. The "1-3 glycosidic bond" may be a β1-3 glycosidic bond if HexA is GlcA, or may be an α1-3 glycosidic bond if HexA is IdoA. The "1-4 glycosidic bond" may be a β1-4 glycosidic bond. In the aforementioned description, each disaccharide does not have a non-specified sulfate group. In the aforementioned description, the expression "containing" includes "consisting of." Thus, for example, a "disaccharide containing a structure represented by [HexA1-3GalN1-4]" may be a "disaccharide consisting of a structure represented by [HexA1-3GalN1-4]." In the aforementioned description, "GalN" may be GalNAc. Thus, for example, a "disaccharide containing a structure represented by [HexA1-3GalN1-4]" may be a "disaccharide containing a structure represented by [HexA1-3GalNAc1-4]" or a "disaccharide consisting of a structure represented by [HexA1-3GalNAc1-4]."

The sulfated CH of the present invention may be a GAG characterized in that, for example, the disaccharide composition ratio of CH-6S is highest among all the disaccharides having a sulfate group (exclusive of CH-0S). In the sulfated CH of the present invention, the disaccharide composition ratio of CH-6S is preferably 10% or higher, more preferably 20% or higher, still more preferably 30% or higher, particularly preferably 40% or higher. In the sulfated CH of the present invention, the disaccharide composition ratio of CH-6S may be 100% or lower, 80% or lower, 60% or lower, or 50% or lower. In the sulfated CH of the present invention, the disaccharide composition ratio of CH-6S falls within the range of disaccharide composition ratio exemplified above in the section "(5) Sulfated GAG of the present invention." In the sulfated CH of the present invention, the disaccharide composition ratio of CH-6S is specifically, for example, 10% to 100%, 20% to 80%, 20% to 60%, 20% to 50%, 30% to 60%, 30% to 50%, or 40% to 50%.

The sulfated CH of the present invention may be a GAG characterized in that, for example, the disaccharide composition ratio of CH-4S is lower than that of CH-6S. In the sulfated CH of the present invention, the disaccharide composition ratio of CH-4S is preferably 5% or lower, more preferably 4% or lower, still more preferably 3% or lower, particularly preferably 2% or lower. In the sulfated CH of the present invention, the disaccharide composition ratio of CH-4S may be 0.1% or higher, 0.2% or higher, 0.5% or higher, or 1% or higher. In the sulfated CH of the present invention, the disaccharide composition ratio of CH-4S falls within the range of disaccharide composition ratio exemplified above in the section "(5) Sulfated GAG of the present invention." In the sulfated CH of the present invention, the disaccharide composition ratio of CH-4S is specifically, for example, 0.1% to 5%, 0.2% to 4%, 0.2% to 3%, 0.2% to 2%, 0.5% to 3%, 0.5% to 2%, or 1% to 2%.

The sulfated CH of the present invention may be a GAG characterized in that, for example, the disaccharide composition ratio of CH-2S is higher than that of CH-4S. In the sulfated CH of the present invention, the disaccharide composition ratio of CH-2S is preferably 3% or higher, more preferably 4% or higher, still more preferably 5% or higher, particularly preferably 6% or higher. In the sulfated CH of the present invention, the disaccharide composition ratio of CH-2S may be 25% or lower, 20% or lower, 15% or lower, or 10% or lower. In the sulfated CH of the present invention, the disaccharide composition ratio of CH-2S falls within the range of disaccharide composition ratio exemplified above in the section "(5) Sulfated GAG of the present invention." In the sulfated CH of the present invention, the disaccharide composition ratio of CH-2S is specifically, for example, 3% to 25%, 4% to 20%, 4% to 15%, 4% to 10%, 5% to 15%, 5% to 10%, or 6% to 10%.

The sulfated CH of the present invention may be a GAG characterized in that, for example, the ratio of the disaccharide composition ratio of CH-2S to that of CH-4S (i.e., 2S/4S ratio) falls within the range described below. In the sulfated CH of the present invention, the 2S/4S ratio is preferably higher than 3, more preferably 3.5 or higher, still more preferably 4 or higher, particularly preferably 5 or higher. In the sulfated CH of the present invention, the 2S/4S ratio may be 20 or lower, 15 or lower, or 10 or lower. In the sulfated CH of the present invention, the 2S/4S ratio is, for example, higher than 3 to 20, higher than 3 to 15, 3.5 to 15, 3.5 to 10, 4 to 10, or 5 to 10.

The sulfated CH of the present invention may be a GAG characterized in that, for example, the disaccharide composition ratio of CH-2S is lower than that of CH-6S. In the sulfated CH of the present invention, the disaccharide composition ratio of CH-2S is preferably 25% or lower, more preferably 20% or lower, still more preferably 15% or lower, particularly preferably 10% or lower. In the sulfated CH of the present invention, the disaccharide composition ratio of CH-2S may be 3% or higher, 4% or higher, 5% or higher, or 6% or higher. In the sulfated CH of the present invention, the disaccharide composition ratio of CH-2S falls within the range of disaccharide composition ratio exemplified above in the section "(5) Sulfated GAG of the present invention." In the sulfated CH of the present invention, the disaccharide composition ratio of CH-2S is specifically, for example, 3% to 25%, 4% to 20%, 4% to 15%, 4% to 10%, 5% to 15%, 5% to 10%, or 6% to 10%.

The sulfated CH: of the present invention may be a GAG characterized in that, for example, the ratio of the disaccharide composition ratio of CH-2S to that of CH-6S (i.e., 2S/6S ratio) falls within the range described below. In the sulfated CH of the present invention, the 2S/6S ratio is preferably 2 or lower, more preferably 1.5 or lower, still more preferably 1 or lower, particularly preferably 0.5 or lower. In the sulfated CH: of the present invention, the 2S/6S ratio may be higher than 0.1, 0.125 or higher, or 0.15 or higher. In the sulfated CH of the present invention, the 2S/6S ratio is, for example, higher than 0.1 to 2, 0.125 to 2, 0.125 to 1.5, 0.15 to 1.5, 0.15 to 1, or 0.15 to 0.5.

The sulfated CH of the present invention may be a GAG characterized in that, for example, the disaccharide composition ratio of CH-$diS_3$ is substantially zero. In the sulfated CH of the present invention, the disaccharide composition ratio of CH-$diS_B$ is preferably 1% or lower, more preferably 0.5% or lower, particularly preferably 0.1% or lower. The sulfated CH of the present invention may be a GAG characterized in that the disaccharide composition ratio of CH-$diS_B$ is zero.

The sulfated CH of the present invention may be a GAG characterized in that, for example, the disaccharide composition ratio of CH-$diS_D$ is higher than that of CH-4S. In the sulfated CH of the present invention, the disaccharide composition ratio of CH-$diS_D$ is preferably 10% or higher, more preferably 15% or higher, still more preferably 20% or higher, particularly preferably 25% or higher. In the sulfated CH of the present invention, the disaccharide composition ratio of CH-$diS_D$ may be 50% or lower, 40% or lower, 35% or lower, or 30% or lower. In the sulfated CH of the present invention, the disaccharide composition ratio of CH-$diS_D$ falls within the range of disaccharide composition ratio exemplified above in the section "(5) Sulfated GAG of the present invention." In the sulfated CH of the present invention, the disaccharide composition ratio of CH-$diS_D$ is specifically, for example, 10% to 50%, 15% to 40%, 15% to 35%, 15% to 30%, 20% to 35%, 20% to 30%, 25% to 30%, 25% to 40%, or 25% to 50%.

In the sulfated CH of the present invention, the disaccharide composition ratio of each of CH-0S, CH-$diS_E$, and CH-triS may be any value. In the sulfated CH of the present invention, the disaccharide composition ratio of CH-0S, CH-$diS_E$, or CH-triS falls within the range of disaccharide composition ratio exemplified above in the section "(5) Sulfated GAG of the present invention."

In the sulfated CH of the present invention, the disaccharide composition ratio can be calculated through determination of the composition ratio of unsaturated disaccharides by, for example, the disaccharide analysis method described in <Referential Example 6> hereinbelow. Specifically, the disaccharide composition ratio of CH-0S can be determined as the composition ratio of $\Delta$Di-0S; the disaccharide composition ratio of CH-6S can be determined as the composition ratio of $\Delta$Di-6S; the disaccharide composition ratio of CH-4S can be determined as the composition ratio of $\Delta$Di-4S; the disaccharide composition ratio of CH-2S can be determined as the composition ratio of $\Delta$Di-2S; the disaccharide composition ratio of CH-$diS_D$ can be determined as the composition ratio of $\Delta$Di-$diS_D$; the disaccharide composition ratio of CH-$diS_E$ can be determined as the composition ratio of $\Delta$Di-$diS_E$; the disaccharide composition ratio of CH-$diS_B$ can be determined as the composition ratio of $\Delta$Di-$diS_3$; and the disaccharide composition ratio of CH-triS can be determined as the composition ratio of $\Delta$Di-triS.

No particular limitation is imposed on the molecular weight of the sulfated CH of the present invention, and the molecular weight may be any value. The molecular weight may be, for example, the molecular weight of the GAG used for the sulfation method of the present invention, which is exemplified above in the section "(1) Sulfation method of the present invention."

No particular limitation is imposed on the sulfation degree of the sulfated CH of the present invention, and the sulfation degree may be any value. The sulfation degree may be, for example, 1% or higher, 5% or higher, 10% or higher, 25% or higher, or 50% or higher. The sulfation degree may be, for example, 400% or lower, 200% or lower, 150% or lower, or 125% or lower. The sulfation degree is preferably, for example, 1% to 400%, 5% to 200%, 10% to 200%, 10% to 150%, 10% to 125%, 25% to 200%, 25% to 150%, 25% to 125%, 50% to 200%, 50% to 150%, or 50% to 125%.

(7) Sulfated Hyaluronic Acid of the Present Invention

In the case where the sulfated GAG of the present invention is a GAG prepared through sulfation of HA (hereinafter referred to as "sulfated HA of the present invention"), the sulfated GAG may be characterized by, for example, the disaccharide composition ratio as described below. In the following description, a disaccharide containing a structure represented by [HexA1-3GlcN1-4] is abbreviated as "HA-0S"; a disaccharide containing a structure represented by [HexA1-3GlcN(6S)1-4] is abbreviated as "HA-6S"; a disaccharide containing a structure represented by [HexA1-3GlcN(4S)1-4] is abbreviated as "HA-4S"; and a disaccharide containing a structure represented by [HexA(2S)1-3GlcN1-4] is abbreviated as "HA-2S." In the aforementioned formulae, "1-3" represents a 1-3 glycosidic bond; "1-4" represents a 1-4 glycosidic bond; "6S" represents a 6-O-sulfate group; "4S" represents a 4-O-sulfate group; and "2S" represents a 2-O-sulfate group. "HexA" may be GlcA or IdoA. The "1-3 glycosidic bond" may be a $\beta$1-3 glycosidic bond if HexA is GlcA, or may be an $\alpha$1-3 glycosidic bond if HexA is IdoA. The "1-4 glycosidic bond" may be a $\beta$1-4 glycosidic bond. In the aforementioned description, the expression "containing" includes "consisting of." Thus, for example, a "disaccharide containing a structure represented by [HexA1-3GlcN1-4]" may be a "disaccharide consisting of a structure represented by [HexA1-3GlcN1-4]." In the aforementioned description, "GlcN" may be GlcNAc. Thus, for example, a "disaccharide containing a structure represented by [HexA1-3GlcN1-4]" may be a "disaccharide containing a structure represented by [HexA1-3GlcNAc1-4]" or a "disaccharide consisting of a structure represented by [HexA1-3GlcNAc1-4]."

The sulfated HA of the present invention may be a GAG characterized by, for example, having HA-4S as a disaccharide component. In the sulfated HA of the present invention, the disaccharide composition ratio of HA-4S may be any value. In the sulfated HA of the present invention, the disaccharide composition ratio of HA-4S may be, for example, 0.001% or higher, 0.01% or higher, 0.1% or higher, 0.5% or higher, 1% or higher, 2% or higher, 3% or higher, 4% or higher, or 5% or higher. The disaccharide composition ratio of HA-4S may be, for example, 25% or lower, 20% or lower, or 15% or lower. In the sulfated HA of the present invention, the disaccharide composition ratio of CH-4S falls within the range of disaccharide composition ratio exemplified above in the section "(5) Sulfated GAG of the present invention." In the sulfated HA of the present invention, the disaccharide composition ratio of HA-4S is specifically, for example, 0.1% to 25%, 1% to 20%, 1% to 15%, 2% to 20%, 2% to 15%, 3% to 20%, 3% to 15%, 4% to 20%, 4% to 15%, 5% to 20%, or 5% to 15%.

In the sulfated HA of the present invention, the disaccharide composition ratio of each of HA-0S, HA-6S, and HA-2S may be any value. In the sulfated HA of the present invention, the disaccharide composition ratio of HA-0S, HA-6S, or HA-2S falls within the range of disaccharide composition ratio exemplified above in the section. "(5) Sulfated GAG of the present invention."

In the sulfated HA of the present invention, the disaccharide composition ratio can be calculated through determination of the composition ratio of unsaturated disaccharides by, for example, the disaccharide analysis method described in <Referential Example 10> hereinbelow. Specifically, the disaccharide composition ratio of HA-0S can be determined as the composition ratio of ΔDiHA-0S; the disaccharide composition ratio of HA-6S can be determined as the composition ratio of ΔDiHA-6S; the disaccharide composition ratio of HA-4S can be determined as the composition ratio of ΔDiHA-4S; and the disaccharide composition ratio of HA-2S can be determined as the composition ratio of ΔDiHA-2S.

No particular limitation is imposed on the molecular weight of the sulfated HA of the present invention, and the molecular weight may be any value. The molecular weight may be, for example, the molecular weight of the GAG used for the sulfat ion method of the present invention, which is exemplified above in the section "(1) Sulfation method of the present invention." The sulfated HA of the present invention may be, for example, a GAG characterized by being a polymer of high molecular weight. The molecular weight may be, for example, 4 MDa (megadalton) or lower, 3.5 MDa or lower, 3 MDa or lower, or 2.5 MDa or lower. The molecular weight may be, for example, 1 MDa or higher, 1.5 MDa or higher, or 2 MDa or higher. The molecular weight is preferably, for example, 1 MDa to 4 MDa, 1 MDa to 3.5 MDa, 1 MDa to 3 MDa, 1 MDa to 2.5 MDa, 1.5 MDa to 4 MDa, 1.5 MDa to 3.5 MDa, 1.5 MDa to 3 MDa, 1.5 MDa to 2.5 MDa, 2 MDa to 4 MDa, 2 MDa to 3.5 MDa, 2 MDa to 3 MDa, or 2 MDa to 2.5 MDa. The term "molecular weight" as used herein refers to a weight average molecular weight. The molecular weight of the sulfated HA can be measured by, for example, any known method. Specifically, the molecular weight of the sulfated HA may be a weight average molecular weight measured by means of, for example, size exclusion chromatography. More specifically, the molecular weight of the sulfated HA can be measured by, for example, the method described in <Referential Example 5> hereinbelow.

Unless otherwise specified, the symbol "%" in terms of the sulfur content described below refers to "mass %." The sulfated HA of the present invention may be a GAG characterized by, for example, the sulfur content as described below. In the sulfated HA of the present invention, the sulfur content may be any value. The sulfur content may be, for example, 10% or lower, 8% or lower, 6% or lower, or 4% or lower. The sulfur content may be, for example, 0.5% or higher, 1% or higher, or 2% or higher. The sulfur content is preferably, for example, 0.5% to 10%, 0.5% to 8%, 0.5% to 6%, 0.5% to 4%, 1% to 10%, 1% to 8%, 1% to 6%, 1% to 4%, 2% to 10%, 2% to 8%, 2% to 6%, or 2% to 4%.

(8) Sulfated Heparosan of the Present Invention

In the case where the sulfated GAG of the present invention is a GAG prepared through sulfation of HPN (hereinafter referred to as "sulfated HPN of the present invention"), the sulfated GAG may be characterized by, for example, the disaccharide composition ratio as described below. In the following description, a disaccharide containing a structure represented by [HexA1-4GlcN1-4] is abbreviated as "HS-0S"; a disaccharide containing a structure represented by [HexA1-4GlcNS1-4] is abbreviated as "HS-NS"; a disaccharide containing a structure represented by [HexA1-4GlcN(6S)1-4] is abbreviated as "HS-6S"; a disaccharide containing a structure represented by [HexA(2S)1-4GlcN1-4] is abbreviated as "HS-2S"; a disaccharide containing a structure represented by [HexA1-4Glc(NS,6S)1-4] is abbreviated as "HS-diS$_1$"; a disaccharide containing a structure represented by [HexA(2S)1-4GlcNS1-4] is abbreviated as "HS-diS$_2$"; a disaccharide containing a structure represented by [HexA(2S)1-4GlcNAc(6S)1-4] is abbreviated as "HS-diS$_3$"; and a disaccharide containing a structure represented by [HexA(2S)1-4Glc(NS,6S)1-4] is abbreviated as "HS-triS." In the aforementioned formulae, "1-4" represents a 1-4 glycosidic bond; "6S" represents a 6-O-sulfate group; "NS" represents an N-sulfate group; and "2S" represents a 2-O-sulfate group. "HexA" may be GlcA or IdoA. The "1-4 glycosidic bond at the reducing terminal of HexA" may be a β1-4 glycosidic bond if HexA is GlcA, or may be an α1-4 glycosidic bond if HexA is IdoA. The "1-4 glycosidic bond at the non-reducing terminal of HexA" may be an α1-4 glycosidic bond. In the aforementioned description, each disaccharide does not have a non-specified sulfate group. In the aforementioned description, the expression "containing" includes "consisting of." Thus, for example, a "disaccharide containing a structure represented by [HexA1-4GlcN1-4]" may be a "disaccharide consisting of a structure represented by [HexA1-4GlcN1-4]." In the aforementioned description, "GlcN" may be GlcNAc. Thus, for example, a "disaccharide containing a structure represented by [HexA1-4GlcN1-4]" may be a "disaccharide containing a structure represented by [HexA1-4GlcNAc1-4]" or a "disaccharide consisting of a structure represented by [HexA1-4GlcNAc1-4]."

In the sulfated HPN of the present invention, the disaccharide composition ratio of each of HS-0S, HS-NS, HS-6S, HS-2S, HS-diS$_1$, HS-diS$_2$, HS-diS$_3$, and HS-triS may be any value. In the sulfated HPN of the present invention, the disaccharide composition ratio of HS-0S, HS-NS, HS-6S, HS-2S, HS-diS$_1$, HS diS$_2$, HS-diS$_3$, or HS-triS falls within the range of disaccharide composition ratio exemplified above in the section "(5) Sulfated GAG of the present invention."

In the sulfated HPN of the present invention, the disaccharide composition ratio can be calculated through determination of the composition ratio of unsaturated disaccharides by, for example, the disaccharide analysis method described in <Referential Example 11> hereinbelow. Specifically, the disaccharide composition ratio of HS-0S can be determined as the composition ratio of ΔDiHS-0S; the disaccharide composition ratio of HS-NS can be determined as the composition ratio of ΔDiHS-NS; the disaccharide composition ratio of HS-6S can be determined as the composition ratio of ΔDiHS-6S; the disaccharide composition ratio of HS-2S can be determined as the composition ratio of ΔDiHS-2S; the disaccharide composition ratio of HS-diS$_1$ can be determined as the composition ratio of ΔDiHS-diS$_1$; the disaccharide composition ratio of HS-diS$_2$ can be determined as the composition ratio of ΔDiHS-diS$_2$; the disaccharide composition ratio of HS-diS$_3$ can be determined as the composition ratio of ΔDiHS-diS$_3$; and the disaccharide composition ratio of HS-triS can be determined as the composition ratio of ΔDiHS-triS.

No particular limitation is imposed on the molecular weight of the sulfated HPN of the present invention, and the molecular weight may be any value. The molecular weight may be, for example, the molecular weight of the GAG used for the sulfation method of the present invention, which is exemplified above in the section "(1) Sulfation method of the present invention."

No particular limitation is imposed on the sulfation degree of the sulfated HPN of the present invention, and the sulfation degree may be any value. The sulfation degree may be, for example, 1% or higher, 5% or higher, 10% or higher, 25% or higher, or 50% or higher. The sulfation degree may be, for example, 400% or lower, 200% or lower, 150% or lower, or 125% or lower. The sulfation degree is preferably, for example, 1% to 400%, 5% to 200%, 10% to 200%, 10% to 150%, 10% to 125%, 25% to 200%, 25% to 150%, 25% to 125%, 50% to 200%, 50% to 150%, or 50% to 125%.

(9) Application of Sulfated GAG of the Present Invention

In one embodiment, the sulfated GAG of the present invention is characterized by having anticoagulant activity similar to that of a GAG having a sulfate group (e.g., HEP or DS). Thus, the sulfated GAG of the present invention may be a glycosaminoglycan characterized by having heparin-like anticoagulant activity; specifically, heparosan characterized by having heparin-like anticoagulant activity. The sulfated GAG of the present invention can be used as, for example, an anticoagulant agent for blood.

In one embodiment, the sulfated GAG of the present invention is characterized in that the disaccharide composition ratio differ from those in any known GAG, such as a GAG derived from an animal, or a GAG sulfated by a method involving the use of an organic solvent. Thus, the sulfated GAG of the present invention is also expected to be a novel useful material.

EXAMPLES

The present invention will next be described in more detail by way of examples, which should not be construed as limiting the technical scope of the invention thereto.

In the examples described below, the sulfation reaction was terminated by neutralizing the sulfation reaction solution to a pH of 6 to 8 through addition of acetic acid or hydrochloric acid.

In the examples described below, the "equivalent" of the amount of a sulfating agent added refers to the mole equivalent thereof.

Among GAGs used in the examples described below, HA and CS were commercially available products (manufactured by SEIKAGAKU CORPORATION), and the other GAGs (CH, dCH, and NAH) were prepared by the methods described below in <Referential Example 1> to <Referential Example 3>.

<Referential Example 1> Preparation of Chondroitin

Chondroitin (CH) was prepared by the method described in the known document (Japanese Kohyo (PCT) Patent Publication No. 2013-520995). Specifically, chondroitin (CH) was prepared through culture of *E. coli* MSC702 strain (constructed by transformation of *E. coli* W3110 strain (ATCC 27325) with the kfoA, kfoB, kfoC, kfoF, and kfoG genes (four copies each) of *E. coli* K4 strain, the kpsF, kpsE, kpsD, kpsU, kpsC, kpsS, kpsM, and kpsT genes (one copy each) of *E. coli* K4 strain, and the xylS gene (one copy) of *Pseudomonas putida*), followed by purification of the resultant culture supernatant.

<Referential Example 2> Preparation of Desulfated Chondroitin Sulfate

Desulfated chondroitin sulfate (dCH) was prepared through desulfation of chondroitin sulfate C (CSC) by the method described in the known document (J. Am. Chem, Soc., 1957, 79 (1), pp. 152-153). The preparation procedures of dCH are as follows.

CSC (derived from shark cartilage, manufactured by SEIKAGAKU CORPORATION) (10 g) was added to a methanol-hydrochloric acid solution (prepared by addition of acetyl chloride (7 mL) to methanol (93 mL)), and the resultant mixture was agitated by means of a magnetic stirrer (hereinafter referred to simply as "stirrer") for 20 hours. Thereafter, the resultant product was subjected to centrifugation, and the precipitate was recovered. The precipitate was dissolved in purified water (100 mL), and the solution was neutralized by addition of an aqueous NaOH solution, followed by dialysis against purified water overnight. The solution was lyophilized, and 0.1 M NaOH was added to the resultant dry powder so as to achieve a concentration of 20 g/L. The resultant solution was agitated by means of a stirrer overnight. The solution was neutralized by addition of HCl, and then dialyzed against purified water overnight. The resultant solution was lyophilized, to thereby yield a lyophilized dCH product. The resultant dCH was found to contain CH-0S (disaccharide composition ratio: 99.8%) and CH-6S (0.2%). No other disaccharides were detected in the GAG.

<Referential Example 3> Preparation of N-Acetylheparosan

N-acetylheparosan (NAH) was prepared by the method described in the known document (Japanese Patent Application Laid-Open (kokai) No. 2004-018840). Specifically, N-acetylheparosan (NAH) was prepared through culture of *E. coli* K5 strain (Serotype O10:K5(L):H4, ATCC 23506), followed by purification of the resultant culture supernatant.

<Referential Example 4> Determination of Molecular Weight of Glycosaminoglycan (1)

The molecular weight (weight average molecular weight) of CH, sulfated CH, HPN, or sulfated HPN was determined by means of size exclusion chromatography under the conditions described below.

The molecular weight of CH, sulfated CH, HPN, or sulfated HPN was determined by means of sequentially connected TSK gel columns G4000PWXL, G3000PWXL, and G2500PWXL (inner diameter: 7.8 mm×length: 300 mm, manufactured by Tosoh Corporation) at a column temperature of 40° C. 0.2 M NaCl was used as a mobile phase, and the flow rate was adjusted to 0.6 mL/min. A differential refractive index detector was used for detection. The molecular weight of a specimen was calculated by use of a calibration curve on the basis of the retention times of peaks obtained through application (100 µL) of a solution of the specimen (concentration: 1 mg/mL). The calibration curve was prepared by use of standards (molecular weight: 52.2 kDa, 31.4 kDa, 20.0 kDa, 10.2 kDa, and 6.57 kDa). The standards were prepared through stepwise ethanol fractionation of CSC (derived from shark cartilage, manufactured by SEIKAGAKU CORPORATION), and their absolute molecular weights were measured by means of the static light scattering method (SLS).

<Referential Example 5> Determination of Molecular Weight of Glycosaminoglycan (2)

The molecular weight (weight average molecular weight) of HA or sulfated HA was determined by means of size exclusion chromatography under the conditions described below.

The molecular weight of HA or sulfated HA was determined by means of a column Ultrahydrogel Linear (inner diameter: 7.8 mm×length: 300 mm, manufactured by Waters) at a column temperature of 40° C. 0.2 M NaCl was used as a mobile phase, and the flow rate was adjusted to 0.6 mL/min. A differential refractive index detector was used for detection. The molecular weight of a specimen was calculated by use of a calibration curve on the basis of the retention times of peaks obtained through application (50 µL) of a solution of the specimen (concentration: 1 mg/mL). The calibration curve was prepared by use of pullulans (5.9 kDa, 11.8 kDa, 22.8 kDa, 47.3 kDa, 112 kDa, 212 kDa, 404 kDa, 788 kDa, 1.22 MDa, and 2.35 MDa, manufactured by SHOWA DENKO K.K.) through the Mark-Houwink correction by the method described in the known document (Yomota C, Miyazaki T, Okada S., Kokuritsu Iyakuhin Shokuhin Eisei Kenkyusho Hokoku. 1999; 117: 135-9.). The Mark-Houwink correction is a method for correcting the molecular weights of heterogeneous polymers by utilizing the phenomenon that the hydrodynamic volume is proportional to the multiplication of intrinsic viscosity $[\eta]$ and weight average molecular weight [Mw]; i.e., two heterogeneous polymers exhibiting the same elution position (retention time) have the same multiplication value of $[\eta]$ and [Mw] in size exclusion chromatography. Thus, even in the case where pullulan is used as a standard material, for example, the molecular weight of HA or sulfated HA can be determined through the Mark-Houwink correction. For the Mark-Houwink correction, the intrinsic viscosity $[\eta]$ of pullulan was calculated by use of the following formula (1), and that of HA was calculated by use of the following formula (2).

$$[\eta]=0.014 Mw^{0.70} \quad (1)$$

$$[\theta]=0.0228 Mw^{0.816} \quad (2)$$

In each of the aforementioned formulae, the "Mw" indicates the weight average molecular weight of the corresponding material. The Mark-Houwink correction was performed by use of the software attached to the HPLC system (Prominence CPC, manufactured by Shimadzu Corporation).

<Referential Example 6> Composition Analysis of Sulfated Chondroitin

For the composition analysis of sulfated CH, the sulfated CH was decomposed by an enzyme, and the resultant disaccharides were subjected to composition analysis (hereinafter referred to as "disaccharide analysis"). The disaccharides were detected by means of HPLC post-column derivatization. The procedures for disaccharide analysis of sulfated CH are described below.

(1) Decomposition of Sulfated Chondroitin

A solution (10 mg/mL) of sulfated CH in purified water was mixed with a half volume of 100 mM Tris-HCl (pH 7.4) and a half volume of a chondroitinase solution (prepared by, addition of 0.1% bovine serum albumin (BSA) to Chondroitinase ABC (manufactured by SEIKAGAKU CORPORATION) to achieve a concentration of 0.1 U/µL), and the resultant solution was allowed to stand still at 37° C. for three hours. The solution was allowed to stand still in boiling water for one minute, and then mixed with a four-fold volume of purified water. The resultant solution was applied to a centrifugal filtration device (Microcon-10, manufactured by Millipore), and the filtrate after centrifugation was recovered as a specimen for disaccharide analysis.

(2) Analysis by HPLC Post-Column Derivatization

The disaccharide analysis was performed by use of a column Senshu Pak DOCOSIL SP100 (inner diameter: 4.6 mm×length: 150 mm, manufactured by Senshu Scientific Co., Ltd.) at a column temperature of 55° C. The eluent was an online-mixed solution of solvent A (purified water), solvent B (200 mM NaCl), solvent C (10 mM tetrabutylammonium), and solvent D (50% acetonitrdle), and the flow rate was adjusted to 1.1 mL/min. The eluate from the column was mixed with a solution of a derivatization reagent (a solution prepared by online-mixing of 0.5% 2-cyanoacetamide and 0.25 M NaOH (1:1)) (flow rate: 0.7 mL/min) by use of a three-way joint. The resultant mixture was passed through a reaction coil (inner diameter: 0.5 mm×length: 10 m), a cooling coil (inner diameter: 0.25 mm×length: 3 m), and a fluorescence detector, in this order. The reaction coil was used at 125° C. The cooling coil was used in distilled water at room temperature. The fluorescence detector was used at an excitation wavelength of 346 nm and a fluorescence wavelength of 410 nm.

The elution was performed in a linear gradient mode wherein the mixing ratio of solvent. B was increased from 1% to 4% (between the initiation of the analysis and 10 minutes after the initiation), increased from 4% to 15% (between 10 minutes and 11 minutes after the initiation), increased from 15% to 25% (between 11 minutes and 20 minutes after the initiation), increased from 25% to 53% (between 20 minutes and 22 minutes after the initiation), and maintained at 53% (between 22 minutes and 29 minutes after the initiation). The mixing ratios of solvents C and D were not varied; i.e., the mixing ratios of solvents C and D were maintained at 12% and 17%, respectively.

(3) Calculation of Disaccharide Composition Ratio

The composition ratio of disaccharide units (hereinafter referred to as "disaccharide composition ratio") was calculated as follows: the specimen prepared in (1) above (10 µL) was applied to the analysis system; the amount by mole of each disaccharide was calculated on the basis of the area of a peak obtained through the analysis described in (2) above by use of a calibration curve; and the amount by mole of the disaccharide was divided by the total amount by mole of all the disaccharides, and the quotient value was expressed in percentage of the disaccharide composition ratio (%). The calibration curve was prepared by use of, as standard materials, chondroitin-sulfate-derived unsaturated disaccharides (ΔDi-0S (hereinafter referred to as "0S"), ΔDi-6S (hereinafter referred to as "6S"), ΔDi-4S (hereinafter referred to as "4S"), ΔDi-2S (hereinafter referred to as "2S"), ΔDi-diS$_D$ (hereinafter referred to as "$diS_D$"), ΔDi-$diS_E$ (hereinafter referred to as "$diS_E$"), and ΔDi-triS (hereinafter referred to as "triS"), manufactured by SEIKAGAKU CORPORATION).

<Referential Example 7> Calculation of Sulfation Degree of Sulfated Chondroitin

The sulfation degree of sulfated CH was calculated by substituting the disaccharide composition ratio calculated in <Referential Example 6> above into the following formula (3).

Sulfation degree (%)=$S_1$+2×$S_2$+3×$S_3$ (3)

In the aforementioned formula, $S_1$ represents the sum of the disaccharide composition ratios of 6S, 4S, and 2S; $S_2$ represents the sum of the disaccharide composition ratios of $diS_D$ and $diS_E$; and $S_3$ represents the disaccharide composition ratio of tris.

<Referential Example 8> Determination of Sulfation Degree of Sulfated Hyaluronic Acid The sulfation degree of sulfated HA was determined through capillary electrophoresis of a specimen prepared by acid hydrolysis of sulfated HA. Specifically, the mole concentrations of sulfate ions and glucosamine (GlcN) contained in a specimen prepared by acid hydrolysis of sulfated HA were determined by means of capillary electrophoresis; the mole concentration of sulfate ions was divided by the mole concentration of GlcN; and the quotient value was expressed in percentage of the sulfation degree (%). The procedures for determination of the sulfation degree of sulfated HA are described below.
(1) Decomposition of Glycosaminoglycan A solution (1 mg/mL) of sulfated HA in purified water was mixed with a three-fold volume of 6N HCl, and the resultant solution was allowed to stand still at 115° C. for three hours for acid hydrolysis. The resultant solution was evaporated to dryness by means of a centrifugal evaporator, and then dissolved in purified water (the amount of purified water was equal to that used for preparation of the sulfated HA solution). The resultant solution was centrifuged to precipitate insoluble matter, and the supernatant was recovered as a specimen for determination of the mole concentrations of GlcN and sulfated ions.
(2) Analysis by Capillary Electrophoresis The mole concentrations of GlcN and sulfated ions were determined by means of Uncoated fused silica capillary (inner diameter: 50 μm×length: 104 cm, manufactured by Agilent) at a temperature of 25° C. Basic Anion Buffer (manufactured by Agilent) was used as a mobile phase, and a voltage of −30 kV was applied. A spectrophotometric detector was used for detection (measurement wavelength: 350 nm, reference wavelength: 230 nm).
(3) Calculation of Sulfation Degree The sulfation degree was calculated as follows: the specimen prepared in (1) above was applied to the analysis system under pressurization at 100 mbar for eight seconds; the mole concentrations of GlcN and sulfated ions were calculated on the basis of the areas of peaks obtained through the analysis described in (2) above by use of a calibration curve; and the mole concentration of sulfate ions was divided by the mole concentration of GlcN, and the quotient value was expressed in percentage of the sulfation degree (%). The calibration curve was prepared by use of a specimen obtained through the treatment (e.g., acid hydrolysis described in (1) above), and GalNAc and sodium sulfate ($Na_2SO_4$) serving as standard materials.

<Referential Example 9> Calculation of Sulfur Content of Sulfated Glycosaminoglycan The sulfur content of sulfated GAG was calculated by substituting the sulfation degree into the following formula (4).

Sulfur content (%)=[(the atomic weight of sulfur)× (sulfation degree/100)]/[(the molecular weight of 0S)+(the molecular weight of $SO_3$)×(sulfation degree/100)]×100 (4)

In the aforementioned formula, the molecular weight of 0S was set to 379.3, the molecular weight of $SO_3$ was set to 80.1, and the atomic weight of sulfur was set to 32.1.

<Referential Example 10> Composition Analysis of Sulfated Hyaluronic Acid

For the composition analysis of sulfated HA, the sulfated HA was decomposed by an enzyme, and the resultant disaccharides were subjected to composition analysis (disaccharide analysis). The procedures for disaccharide analysis of sulfated HA are described below.
(1) Decomposition of Sulfated Hyaluronic Acid A solution (10 mg/mL) of sulfated HA in purified water was mixed with a half volume of 100 mM Tris-HCl (pH 7.4) and a half volume of a chondroitinase solution (prepared by addition of 0.1% bovine serum albumin (BSA) to Chondroitinase ABC (manufactured by SEIKAGAKU CORPORATION) to achieve a concentration of 0.1 U/μL), and the resultant solution was allowed to stand still at 37° C. for three hours. The solution was allowed to stand still in boiling water for one minute, and then mixed with a four-fold volume of purified water. The resultant solution was applied to a centrifugal filtration device (Microcon-10, manufactured by Millipore), and the filtrate after centrifugation was recovered as a specimen for disaccharide analysis.
(2) HPLC analysis The disaccharide analysis was performed by use of a column UK-Amino (inner diameter: 4.6 mm×length: 150 mm, manufactured by Senshu Scientific Co., Ltd.) at a column temperature of 60° C. The eluent was an online-mixed solution of solvent A (purified water) and solvent B (0.8 M $NaH_2PO_4$), and the flow rate was adjusted to 1 mL/min. A spectrophotometric detector was used for detection (measurement wavelength: 232 nm).

The elution was performed in a linear gradient mode wherein the mixing ratio of solvent B was increased from 2% to 65% (between the initiation of the analysis and 20 minutes after the initiation).
(3) Calculation of Disaccharide Composition Ratio The disaccharide composition ratio was calculated as follows: the specimen prepared in (1) above (10 μL) was applied to the analysis system; the amount by mole of each disaccharide was determined on the basis of the area of a peak obtained through the analysis described in (2) above by use of a calibration curve; and the amount by mole of the disaccharide was divided by the total amount by mole of all the disaccharides, and the quotient value was expressed in percentage of the disaccharide composition ratio (%). The calibration curve was prepared by use of, as standard materials, sulfated-hyaluronic-acid-derived unsaturated disaccharides (ΔDiHA-0S (hereinafter referred to as "0S"), ΔDiHA-6S (hereinafter referred to as "6S"), ΔDiHA-4S (hereinafter referred to as "4S"), and ΔDiHA-2S (hereinafter referred to as "2S")). The sulfated-hyaluronic-acid-derived unsaturated disaccharides were prepared as follows: HA sulfated by the sulfation method of the present invention was decomposed into disaccharides by the method described in (1) above; the disaccharides were subjected to anion-exchange chromatography and size exclusion chromatography; and the bonding positions of sulfate groups were identified by mass analysis and NMR.

<Referential Example 11> Composition Analysis of Sulfated Heparosan

For the composition analysis of sulfated heparosan, the sulfated heparosan was decomposed by an enzyme, and the resultant disaccharides were subjected to composition analysis (disaccharide analysis). The disaccharides were detected by means of HPLC post-column derivatization. The procedures for disaccharide analysis of sulfated heparosan are described below.
(1) Decomposition of Sulfated Heparosan A solution (10 mg/mL) of sulfated heparosan in purified water was mixed with a half volume of 20 mM aqueous sodium acetate solution (pH 7.0)/2 mM calcium acetate and a half volume of EM II solution (prepared by addition of 0.1% ESA to achieve 3 mU/μL heparitinase I, 2 mU/μL heparitinase II, and 5 mU/μL heparinase (manufactured by SEIKAGAKU CORPORATION)), and the resultant solution was allowed to stand still at 37° C. for three hours. The solution was allowed to stand still in boiling water for one minute, and then mixed with a four-fold volume of purified water. The resultant solution was applied to a centrifugal filtration device (Microcon-10, manufactured by Millipore), and the filtrate after centrifugation was recovered as a specimen for disaccharide analysis.
(2) Analysis by HPLC Post-Column Derivatization The disaccharide analysis was performed under the same conditions as described in the section "(2) Analysis by HPLC post-column derivatization" of <Referential Example 6>.
(3) Calculation of Disaccharide Composition Ratio The disaccharide composition ratio was calculated as follows: the specimen prepared in (1) above (10 μL) was applied to the analysis system; the amount by mole of each disaccharide was determined on the basis of the area of a peak obtained through the analysis described in (2) above by use of a calibration curve; and the amount by mole of the disaccharide was divided by the total amount by mole of all the disaccharides, and the quotient value was expressed in percentage of the disaccharide composition ratio (%). The calibration curve was prepared by use of, as standard materials, heparin- or heparan-sulfate-derived unsaturated disaccharides (ΔDiHS-0S (hereinafter referred to as "0S"), ΔDiHS-NS (hereinafter referred to as "NS"), ΔDiHS-6S (hereinafter referred to as "6S"), ΔDiHS-diS$_1$ (hereinafter referred to as "diS$_1$"), ΔDiHS-diS$_2$ (hereinafter referred to as "diS$_2$"), and ΔDiHS-triS (hereinafter referred to as "triS"), manufactured by SEIKAGAKU CORPORATION).

<Referential Example 12> Calculation of Sulfur Content of Alkylated Sulfated Chondroitin The sulfur content of alkylated sulfated CH was determined through capillary electrophoresis of a specimen prepared by acid hydrolysis of the sulfated CH. Specifically, the mole concentration of sulfate ions contained in a specimen prepared by acid hydrolysis of alkylated sulfated CH was determined by means of capillary electrophoresis, and then the sulfur content was calculated from the following formula (5).

Sulfur content (%)=(the atomic weight of sulfur)/(the molecular weight of sulfate ions)×(the concentration of sulfate ions)/(the concentration of GAG)×100     (5)

In the aforementioned formula, the atomic weight of sulfur was set to 32.1, and the molecular weight of sulfate ions was set to 96.1. In the aforementioned formula, the concentration of GAG was obtained by dividing the dry weight of alkylated sulfated CH by the amount of the sample solution.

In the aforementioned method, the determination by means of acid hydrolysis and capillary electrophoresis was performed under the same conditions as described in <Referential Example 8>.

<Referential Example 13> Calculation of Sulfation Degree of Sulfated Heparosan

The sulfation degree of sulfated HPN was calculated by substituting the disaccharide composition ratio calculated in <Referential Example 11> above into the following formula (6).

Sulfation degree (%)=$S_1$+2×$S_2$+3×$S_3$     (6)

In the aforementioned formula, $S_1$ represents the sum of the disaccharide composition ratios of NS, 6S, and 2S; $S_2$ represents the sum of the disaccharide composition ratios of $diS_1$, $diS_2$, and $diS_3$; and $S_3$ represents the disaccharide composition ratio of tris.

<Example 1> Examination of Mole Concentration of Strong Base (1)

$Na_2SO_4$ and an aqueous NaOH solution (0.1 M to 4 M) were added to CH (35.8 kDa) to prepare a solution having a CH concentration of 100 mg/mL (10% w/v) and a $Na_2SO_4$ concentration of 500 mg/mL. The solution was heated to 40° C. and a sulfur trioxide-trimethylamine complex (TMA-$SO_3$) (manufactured by Sigma-Aldrich) (2.9 equivalents, equal to the concentration of CH in terms of weight concentration (w/v)) was added to the solution. Thereafter, the resultant solution was agitated by means of a stirrer for one hour for sulfation reaction. After the termination of the reaction, the resultant solution was mixed with a three-fold volume of purified water and then dialyzed against purified water for two days. The resultant solution was neutralized by addition of an aqueous NaOH solution and then lyophilized, to thereby yield a dry powder. The resultant sulfated CH was subjected to disaccharide analysis, to thereby calculate the sulfation degree. The results are illustrated in Table 1 and FIG. 1.

TABLE 1

| NaOH | Disaccharide composition ratio (%) | | | | | | | Sulfation degree |
|---|---|---|---|---|---|---|---|---|
| (M) | 0S | 6S | 4S | 2S | $diS_D$ | $diS_E$ | triS | (%) |
| 0.1 | 96.4 | 3.0 | 0.1 | 0.6 | 0.0 | 0.0 | 0.0 | 4 |
| 0.25 | 87.8 | 10.1 | 0.2 | 1.9 | 0.0 | 0.0 | 0.0 | 12 |
| 0.5 | 75.0 | 19.6 | 0.4 | 3.6 | 1.2 | 0.2 | 0.0 | 26 |
| 0.75 | 64.7 | 26.9 | 0.6 | 4.7 | 2.7 | 0.4 | 0.0 | 38 |
| 1 | 57.0 | 31.9 | 0.8 | 5.4 | 4.3 | 0.7 | 0.0 | 48 |
| 2 | 54.4 | 33.2 | 0.9 | 5.4 | 5.1 | 1.0 | 0.0 | 52 |

TABLE 1-continued

| NaOH | Disaccharide composition ratio (%) | | | | | | | Sulfation degree |
|---|---|---|---|---|---|---|---|---|
| (M) | 0S | 6S | 4S | 2S | $diS_D$ | $diS_E$ | triS | (%) |
| 3 | 60.4 | 29.1 | 0.9 | 4.8 | 3.9 | 1.0 | 0.0 | 45 |
| 4 | 62.6 | 27.9 | 1.0 | 4.6 | 3.1 | 0.9 | 0.0 | 42 |

The sulfated CH produced by the sulfation method of the present invention exhibited a disaccharide composition ratio of CH-$diS_B$ of lower than 0.1%. Thus, description of data on CH-$diS_B$ is omitted in the table. In subsequent Examples, description of data on CH-$diS_B$ will be omitted in tables.

As is shown in Table 1, it was confirmed that, by the examination using CH, the coexistence of a GAG and a sulfating agent in a strongly basic solution could lead to sulfation of the GAG. It was also found that appropriate adjustment of the mole concentration of a strong base could lead to production of a sulfated GAG exhibiting a desired sulfation degree.

<Example 2> Examination of Mole Concentration of Strong Base (2)

$Na_2SO_4$ and an aqueous NaOH solution (0.5 M to 4 M) were added to HA (800 kDa) to prepare a solution having an HA concentration of 10 mg/mL (1% w/v) and a $Na_2SO_4$ concentration of 100 mg/mL. The solution was heated to 40° C. and TMA-$SO_3$ (58 equivalents, 20 times the concentration of HA in terms of weight concentration (w/v)) was added to the solution. Thereafter, the resultant solution was agitated by means of a stirrer for three hours for sulfation reaction. After the termination of the reaction, the resultant solution was mixed with an equiamount of purified water and then dialyzed against purified water overnight. The resultant solution was neutralized by addition of an aqueous NaOH solution and then lyophilized, to thereby yield a dry powder. The sulfation degree of the resultant sulfated HA was determined, to thereby calculate the sulfur content. The results are illustrated in Table 2.

TABLE 2

| NaOH (M) | Sulfation degree (%) | Sulfur content (%) |
|---|---|---|
| 0.05 | 2 | 0.2 |
| 0.1 | 4 | 0.4 |
| 0.5 | 37 | 2.9 |
| 1 | 70 | 5.3 |
| 2 | 43 | 3.4 |
| 3 | 34 | 2.7 |
| 4 | 30 | 2.4 |

As is shown in Table 2, it was confirmed that a GAG could be sulfated even in the case where the GAG is HA.

<Example 3> Examination of Mole Concentration of Strong Base (3)

$Na_2SO_4$ and an aqueous NaOH solution (0.05 M to 2 M) were added to CH (35.8 kDa) to prepare a solution having a CH concentration of 100 mg/mL (10% w/v) and a $Na_2SO_4$ concentration of 500 mg/mL. The solution was heated to 40° C. and TMA-$SO_3$ (2.9 equivalents) was added to the solution. Thereafter, the resultant solution was agitated by means of a stirrer for five minutes for sulfation reaction. After the termination of the reaction, the resultant solution was mixed with a three-fold volume of purified water and then dialyzed against purified water for two days. The resultant solution was neutralized by addition of an aqueous NaOH solution and then lyophilized, to thereby yield a dry powder. The resultant sulfated CH was subjected to disaccharide analysis, to thereby calculate the sulfation degree. The results are illustrated in Table 3.

TABLE 3

| NaOH (M) | pH | Sulfation degree (%) |
|---|---|---|
| 0.05 | 11.5 | 1 |
| 0.1 | 11.7 | 2 |
| 2 | 13.1 | 50 |

The pH illustrated in Table 3 corresponds to the pH of the sulfation reaction solution measured at the time of completion of the reaction (i.e., five minutes after addition of the sulfating agent). As is shown in Table 3, it was confirmed that the coexistence of a GAG and a sulfating agent in a solution at a pH of 11.5 or higher could lead to sulfation of the GAG.

<Example 4> Examination of Reaction Temperature $Na_2SO_4$ and 2 M aqueous NaOH solution were added to CH (41.8 kDa) to prepare a solution having a CH concentration of 200 mg/mL (20% w/v) and a $Na_2SO_4$ concentration of 500 mg/mL. The solution was heated or cooled to a temperature of 0 to 60° C. and TMA-$SO_3$ (2.9 equivalents) was added to the solution. Thereafter, the resultant solution was agitated by means of a stirrer for one hour for sulfation reaction. After the termination of the reaction, the resultant solution was mixed with a three-fold volume of purified water and then dialyzed against purified water for two days. The resultant solution was neutralized by addition of an aqueous NaOH solution and then lyophilized, to thereby yield a dry powder. The resultant sulfated CH was subjected to disaccharide analysis, to thereby calculate the sulfation degree. In addition, the molecular weight of the sulfated CH was measured. The results are illustrated in Table 4.

TABLE 4

| Temperature | Disaccharide composition ratio (%) | | | | | | | Sulfation degree | Molecular weight |
|---|---|---|---|---|---|---|---|---|---|
| (° C.) | 0S | 6S | 4S | 2S | $diS_D$ | $diS_E$ | triS | (%) | (kDa) |
| 0 | 74.7 | 19.5 | 0.4 | 3.9 | 1.2 | 0.2 | 0.0 | 27 | 31.1 |
| 25 | 31.6 | 41.4 | 1.3 | 7.9 | 13.7 | 2.2 | 1.9 | 88 | 31.2 |
| 50 | 29.9 | 38.8 | 1.5 | 8.8 | 16.0 | 2.6 | 2.4 | 94 | 29.2 |
| 60 | 35.6 | 36.5 | 1.6 | 9.1 | 13.3 | 2.1 | 1.8 | 83 | 30.2 |

As is shown in Table 4, it was confirmed that a GAG could be sulfated at any reaction temperature. It was also found that appropriate adjustment of the reaction temperature could lead to production of a sulfated GAG exhibiting a desired sulfation degree. In one embodiment, sulfated CH (i.e., a GAG prepared through sulfation of CH) is characterized by containing CH-6S in the highest disaccharide composition ratio. This characteristic feature is common with chondroitin sulfate C (CSC). Thus, it was also found that the method of the present invention could prepare a CSC-like polysaccharide.

<Example 5> Examination of Concentration of Glycosaminoglycan (1)

$Na_2SO_4$ and 2 M aqueous NaOH solution were added to CH (30.2 kDa) to prepare a solution having a CH concentration of 10 to 66.7 mg/mL (1 to 6.67% w/v) and a $Na_2SO_4$ concentration of 500 mg/mL. The solution was heated to 40° C. and $TMA-SO_3$ (2.9 equivalents) was added to the solution. Thereafter, the resultant solution was agitated by means of a stirrer for one hour for sulfation reaction. After the termination of the reaction, the resultant solution was mixed with a three-fold volume of purified water and then dialyzed against purified water for two days. The resultant solution was neutralized by addition of an aqueous NaOH solution and then lyophilized, to thereby yield a dry powder. The resultant sulfated CH was subjected to disaccharide analysis, to thereby calculate the sulfation degree. In addition, the molecular weight of the sulfated CH was measured. The results are illustrated in Table 5.

TABLE 5

| Concentration | Disaccharide composition ratio (%) | | | | | | | Sulfation degree | Molecular weight |
|---|---|---|---|---|---|---|---|---|---|
| (w/v) | 0S | 6S | 4S | 2S | $diS_D$ | $diS_E$ | triS | (%) | (kDa) |
| 1 | 93.9 | 5.0 | 0.1 | 0.9 | 0.1 | 0.0 | 0.0 | 6 | 26.3 |
| 2.5 | 86.0 | 11.2 | 0.3 | 2.0 | 0.4 | 0.1 | 0.0 | 15 | 26.6 |
| 5 | 74.1 | 20.3 | 0.5 | 3.4 | 1.4 | 0.3 | 0.0 | 28 | 27.2 |
| 6.67 | 65.8 | 26.0 | 0.6 | 4.3 | 2.7 | 0.6 | 0.0 | 38 | 27.0 |

As is shown in Table 5, it was confirmed that, by the examination using CH, a GAG could be sulfated at any GAG concentration. It was also found that appropriate adjustment of the GAG concentration could lead to production of a sulfated GAG exhibiting a desired sulfation degree.

<Example 6> Examination of Concentration of Glycosaminoglycan (2)

$Na_2SO_4$ and 2 M aqueous NaOH solution were added to a solution of HA (2.7 MDa) in purified water to prepare a solution having a final HA concentration of 1 to 10 mg/mL (0.1 to 1% w/v), a final $Na_2SO_4$ concentration of 80 mg/mL, and a final NaOH concentration of 1 M. The solution was cooled to 4° C. and $TMA-SO_3$ (58 equivalents) was added to the solution. Thereafter, the resultant solution was agitated by means of a stirrer for 18 hours for sulfation reaction. After the termination of the reaction, the resultant solution was mixed with a two-fold volume of purified water and then dialyzed against purified water for two days. The resultant solution was neutralized by addition of an aqueous NaOH solution and then lyophilized, to thereby yield a dry powder. The sulfation degree of the resultant sulfated HA was determined, to thereby calculate the sulfur content. In addition, the molecular weight of the sulfated HA was measured. The results are illustrated in Table 6.

TABLE 6

| Concentration (w/v) | Sulfation degree (%) | Molecular weight (MDa) | Sulfur content (%) |
|---|---|---|---|
| 0.1 | 11 | 2.3 | 0.9 |
| 0.5 | 36 | 2.1 | 2.8 |
| 1 | 37 | 2.2 | 2.9 |

As is shown in Table 6, it was confirmed that a GAG could be sulfated at any GAG concentration even in the case where the GAG is HA. It was also confirmed that, in one embodiment, the sulfated HA (GAG) prepared by the sulfation method of the present invention had a molecular weight of 2 MDa or higher even after the sulfation reaction.

<Example 7> Examination of Reaction Time (1)

$Na_2SO_4$ and 2 M aqueous NaOH solution were added to CH (41.8 kDa) to prepare a solution having a CH concentration of 200 mg/mL (20% w/v) and a $Na_2SO_4$ concentration of 500 mg/mL. The solution was heated to 40° C. and $TMA-SO_3$ (2.9 equivalents) was added to the solution. Thereafter, the resultant solution was agitated by means of a stirrer for a predetermined period of time (one to nine hours) for sulfation reaction. After the termination of the reaction, the resultant solution was mixed with a three-fold volume of purified water and then dialyzed against purified water for two days. The resultant solution was neutralized by addition of an aqueous NaOH solution and then lyophilized, to thereby yield a dry powder. The resultant sulfated CH was subjected to disaccharide analysis, to thereby calculate the sulfation degree. In addition, the molecular weight of the sulfated CH was measured. The results are illustrated in Table 7.

TABLE 7

| Time | Disaccharide composition ratio (%) | | | | | | | Sulfation degree | Molecular weight |
|---|---|---|---|---|---|---|---|---|---|
| (hour) | 0S | 6S | 4S | 2S | $diS_D$ | $diS_E$ | triS | (%) | (kDa) |
| 1 | 25.3 | 41.0 | 1.4 | 8.1 | 18.2 | 3.0 | 3.0 | 102 | 30.4 |
| 3 | 23.5 | 40.8 | 1.4 | 7.9 | 19.3 | 3.3 | 3.7 | 107 | 31.4 |

TABLE 7-continued

| Time | Disaccharide composition ratio (%) | | | | | | | Sulfation degree | Molecular weight |
|---|---|---|---|---|---|---|---|---|---|
| (hour) | 0S | 6S | 4S | 2S | $diS_D$ | $diS_E$ | triS | (%) | (kDa) |
| 6 | 22.9 | 40.7 | 1.4 | 7.8 | 19.9 | 3.4 | 3.9 | 108 | 31.4 |
| 9 | 22.6 | 41.1 | 1.4 | 7.9 | 19.8 | 3.4 | 3.8 | 108 | 30.3 |

As is shown in Table 7, it was confirmed that, by the examination using CH, any reaction time could be used for sulfation of a GAG.

<Example 8> Examination of Reaction Time (2)

$Na_2SO_4$ and 2 M aqueous NaOH solution were added to a solution of HA (2.7 MDa) in purified water to prepare a solution having a final HA concentration of 1 mg/mL (0.1% w/v), a final $Na_2SO_4$ concentration of 80 mg/mL, and a final NaOH concentration of 1 M. The solution was cooled to 4° C. and TMA-$SO_3$ (58 equivalents) was added to the solution. Thereafter, the resultant solution was agitated by means of a stirrer for a predetermined period of time (one to seven days) for sulfation reaction. After the termination of the reaction, the resultant solution was mixed with a two-fold volume of purified water and then dialyzed against purified water for two days. The resultant solution was neutralized by addition of an aqueous NaOH solution and then lyophilized, to thereby yield a dry powder. The sulfation degree of the resultant sulfated HA was determined, to thereby calculate the sulfur content. The results are illustrated in Table 8.

TABLE 8

| Reaction time | Sulfation degree (%) | Sulfur content (%) |
|---|---|---|
| 1 day | 11 | 0.9 |
| 7 days | 18 | 1.5 |

As is shown in Table 8, it was confirmed that any reaction time could be used for sulfation of a GAG even in the case where the GAG is HA.

<Example 9> Examination of Additive Amount of Sulfating Agent (1)

$Na_2SO_4$ and 2 M aqueous NaOH solution were added to CH (41.8 kDa) to prepare a solution having a CH concentration of 200 mg/mL (20% w/v) and a $Na_2SO_4$ concentration of 500 mg/mL. The solution was heated to 40° C. and TMA-$SO_3$ (0.3 to 2.9 equivalents) was added to the solution. Thereafter, the resultant solution was agitated by means of a stirrer for 20 hours for sulfation reaction. After the termination of the reaction, the resultant solution was mixed with a 1.5-fold volume of purified water and then dialyzed against purified water for two days. The resultant solution was neutralized by addition of an aqueous NaOH solution and then lyophilized, to thereby yield a dry powder. The resultant sulfated CH was subjected to disaccharide analysis, to thereby calculate the sulfation degree. The results are illustrated in Table 9.

TABLE 9

| Sulfating agent (Mole equivalents) | Disaccharide composition ratio (%) | | | | | | | Sulfation degree (%) |
|---|---|---|---|---|---|---|---|---|
| | 0S | 6S | 4S | 2S | $diS_D$ | $diS_E$ | triS | |
| 0.3 | 86.1 | 11.2 | 0.5 | 1.5 | 0.4 | 0.2 | 0.1 | 15 |
| 0.9 | 63.0 | 28.1 | 1.2 | 4.2 | 2.6 | 0.7 | 0.3 | 41 |
| 2.0 | 27.7 | 42.0 | 1.6 | 7.4 | 15.6 | 3.1 | 2.6 | 96 |
| 2.9 | 18.8 | 40.4 | 1.6 | 7.0 | 22.2 | 4.2 | 5.8 | 119 |

As is shown in Table 9, it was confirmed that, by the examination using CH, a GAG could be sulfated through addition of any amount of a sulfating agent. It was also found that appropriate adjustment of the additive amount of a sulfating agent could lead to production of a sulfated GAG exhibiting a desired sulfation degree.

<Example 10> Examination of Additive Amount of Sulfating Agent (2)

$Na_2SO_4$ and 2 M aqueous NaOH solution were added to a solution of HA (2.7 MDa) in purified water to prepare a solution having a final HA concentration of 1 mg/mL (0.1% w/v), a final $Na_2SO_4$ concentration of 80 mg/mL, and a final NaOH concentration of 1 M. The solution was cooled to 4° C. and TMA-$SO_3$ (29 to 116 mole equivalents) was added to the solution. Thereafter, the resultant solution was agitated by means of a stirrer for 18 hours for sulfation reaction. After the termination of the reaction, the resultant solution was mixed with a two-fold volume of purified water and then dialyzed against purified water for two days. The resultant solution was neutralized by addition of an aqueous NaOH solution and then lyophilized, to thereby yield a dry powder. The sulfation degree of the resultant sulfated HA was determined, to thereby calculate the sulfur content. The results are illustrated in Table 10.

TABLE 10

| Sulfating agent (Mole equivalents) | Sulfation degree (%) | Sulfur content (%) |
|---|---|---|
| 29 | 6 | 0.5 |
| 58 | 11 | 0.9 |
| 116 | 20 | 1.7 |

As is shown in Table 10, it was confirmed that a GAG could be sulfated through addition of any amount of a sulfating agent even in the case where the GAG is HA.

<Example 11> Examination of Type of Strong Base $Na_2SO_4$ and 1 M strongly basic aqueous solution (aqueous NaOH solution, aqueous KOH solution, or aqueous LiOH solution) were added to HA (800 kDa) to prepare a solution having a final HA concentration of 1 mg/mL (0.1% w/v) and a final $Na_2SO_4$ concentration of 100 mg/mL. The solution was cooled to 4° C. and TMA-SO₃ (58 equivalents) was added to the solution. Thereafter, the resultant solution was agitated by means of a stirrer for 18 hours for sulfation reaction. After the termination of the reaction, the resultant solution was mixed with a two-fold volume of purified water and then dialyzed against purified water for two days. The resultant solution was neutralized by addition of an aqueous NaOH solution and then lyophilized, to thereby yield a dry powder. The sulfation degree of the resultant sulfated HA was determined, to thereby calculate the sulfur content. The results are illustrated in Table 11.

TABLE 11

| Solvent | Sulfation degree (%) | Sulfur content (%) |
|---|---|---|
| NaOH | 11 | 0.9 |
| KOH | 12 | 1.0 |
| LiOH | 12 | 1.0 |

As is shown in Table 11, it was confirmed that a GAG could be sulfated even in the case where an aqueous KOH solution or an aqueous LiOH solution was used as a strongly basic solution.

<Example 12> Examination of Type of Sulfating Agent (1)

Na₂SO₄ and 2 M aqueous NaOH solution were added to CH (41.8 kDa) to prepare a solution having a CH concentration of 200 mg/mL (20% w/v) and a Na₂SO₄ concentration of 500 mg/mL. The solution was heated to 40° C. and a sulfur trioxide-pyridine complex (Pyr-SO₃, manufactured by Tokyo Chemical Industry Co., Ltd.) (2.9 equivalents) was added to the solution. Thereafter, the resultant solution was agitated by means of a stirrer for one hour for sulfation reaction. After the termination of the reaction, the resultant solution was mixed with a three-fold volume of purified water and then dialyzed against purified water for two days. The resultant solution was neutralized by addition of an aqueous NaOH solution and then lyophilized, to thereby yield a dry powder. The resultant sulfated CH was subjected to disaccharide analysis, to thereby calculate the sulfation degree. The results are illustrated in Table 12.

TABLE 12

| Sulfating agent | Disaccharide composition ratio (%) | | | | | | | Sulfation degree (%) |
|---|---|---|---|---|---|---|---|---|
| | 0S | 6S | 4S | 2S | diS$_D$ | diS$_E$ | triS | |
| Pyr-SO₃ | 70.6 | 16.4 | 1.2 | 8.2 | 3.0 | 0.5 | 0.2 | 33 |

As is shown in Table 12, it was confirmed that a GAG could be sulfated even in the case where Pyr-SO₃ is used as a sulfating agent.

<Example 13> Examination of Type of Sulfating Agent (2)

2 M aqueous NaOH solution was added to CH (41.8 kDa) to prepare a solution having a CH concentration of 100 mg/mL (10% w/v). The solution was heated to 40° C. and a sulfur trioxide-dimethylethylamine complex (DMEA-SO₃, prepared by addition of a solvent mixture of chlorosulfonic acid (10 mL) and chloroform (20 mL) to a solvent mixture of dimethylethylamine (100 mL) and chloroform (100 mL) under ice cooling) (2.9 equivalents) was added to the solution. Thereafter, the resultant solution was agitated by means of a stirrer for one hour for sulfation reaction. After the termination of the reaction, the resultant solution was mixed with a three-fold volume of purified water and then dialyzed against purified water for two days. The resultant solution was neutralized by addition of an aqueous NaOH solution and then lyophilized, to thereby yield a dry powder. The resultant sulfated CH was subjected to disaccharide analysis, to thereby calculate the sulfation degree. The results are illustrated in Table 13.

TABLE 13

| Sulfating agent | Disaccharide composition ratio (%) | | | | | | | Sulfation degree (%) |
|---|---|---|---|---|---|---|---|---|
| | 0S | 6S | 4S | 2S | diS$_D$ | diS$_E$ | triS | |
| DMEA-SO₃ | 58.8 | 28.8 | 1.4 | 5.9 | 4.3 | 0.8 | 0.0 | 46 |

As is shown in Table 13, it was confirmed that a GAG could be sulfated even in the case where DMEA-SO₃ is used as a sulfating agent.

<Example 14> Examination of Mole Concentration of Strong Base (4)

Na₂SO₄ and an aqueous NaOH solution (2 M or 3 M) were added to HA (800 kDa) to prepare a solution having an HA concentration of 10 mg/mL (1% w/v) and a Na₂SO₄ concentration of 80 mg/mL. The solution was cooled to 4° C. and TMA-SO₃ (58 equivalents) was added to the solution. Thereafter, the resultant solution was agitated by means of a stirrer for 18 hours for sulfation reaction. After the termination of the reaction, the resultant solution was mixed with a two-fold volume of purified water and then dialyzed against purified water overnight. The resultant solution was neutralized by addition of an aqueous NaOH solution and then lyophilized, to thereby yield a dry powder. The sulfation degree of the resultant sulfated HA was determined, to thereby calculate the sulfur content. The results are illustrated in Table 14.

TABLE 14

| NaOH (M) | Sulfation degree (%) | Sulfur content (%) |
|---|---|---|
| 1 | 11 | 0.9 |
| 2 | 55 | 4.2 |
| 3 | 90 | 6.4 |

As is shown in Table 14, in the case of a reaction temperature of 4° C., it was confirmed that a NaOH concentration of 2 M or 3 M could lead to sulfation reaction efficiency higher than that in case of a NaOH concentration of 1 M (i.e., the concentration exhibiting the highest sulfation reaction efficiency at a reaction temperature of 40° C., see Table 2).

<Example 15> Examination of Additive Amount of Sodium Sulfate

Na₂SO₄ and 2 M aqueous NaOH solution were added to CH (41.8 kDa) to prepare a solution having a CH concentration of 200 mg/mL (20% w/v) and a Na₂SO₄ concentration of 200 to 600 mg/mL. Separately, only 2 M aqueous NaOH solution was added to CH to prepare a solution containing no Na$_2$SO$_4$. Each of these solutions was heated to 40° C. and TMA-SO$_3$ (2.9 equivalents) was added to the solution. Thereafter, the resultant solution was agitated by means of a stirrer for one hour for sulfation reaction. After the termination of the reaction, the resultant solution was mixed with a three-fold volume of purified water and then dialyzed against purified water for two days. The resultant solution was neutralized by addition of an aqueous NaOH solution and then lyophilized, to thereby yield a dry powder. The resultant sulfated CH was subjected to disaccharide analysis, to thereby calculate the sulfation degree. In addition, the molecular weight of the sulfated CH was measured. The results are illustrated in Table 15.

TABLE 15

| Na$_2$SO$_4$ (mg/mL) | Disaccharide composition ratio (%) | | | | | | | Sulfation degree (%) | Molecular weight (kDa) |
|---|---|---|---|---|---|---|---|---|---|
| | 0S | 6S | 4S | 2S | diS$_D$ | diS$_E$ | triS | | |
| 0 | 27.5 | 42.8 | 1.4 | 7.7 | 16.3 | 2.3 | 2.0 | 95 | 31.5 |
| 200 | 26.0 | 41.7 | 1.5 | 7.9 | 17.6 | 2.8 | 2.6 | 95 | 31.2 |
| 400 | 25.6 | 41.4 | 1.5 | 8.1 | 17.8 | 2.9 | 2.8 | 101 | 30.3 |
| 600 | 27.1 | 40.6 | 1.5 | 8.2 | 17.1 | 2.8 | 2.7 | 100 | 29.4 |

As is shown in Table 15, it was confirmed that a GAG could be sulfated regardless of the additive amount of sodium sulfate. It was also confirmed that no coexistence with a sulfate salt (e.g., sodium sulfate) is preferred for preventing a reduction in molecular weight accompanied by the sulfation reaction.

<Example 16> Examination of Sulfation of GAG Having Sulfate Group (1)

2 M aqueous NaOH solution was added to chondroitin sulfate A (CSA) (20.1 kDa) to prepare a solution having a CSA concentration of 200 mg/mL (20% w/v). The solution was heated to 40° C. and TMA-SO$_3$ (2.9 equivalents) was added to the solution. Thereafter, the resultant solution was agitated by means of a stirrer for one hour for sulfation reaction. After the termination of the reaction, the resultant solution was mixed with a three-fold volume of purified water and then dialyzed against purified water for two days. The resultant solution was neutralized by addition of an aqueous NaOH solution and then lyophilized, to thereby yield dry powder. The resultant sulfated CS was subjected to disaccharide analysis, to thereby calculate the sulfation degree. The results are illustrated in Table 16.

TABLE 16

| | Disaccharide composition ratio (%) | | | | | | | Sulfation degree (%) |
|---|---|---|---|---|---|---|---|---|
| | 0S | 6S | 4S | 2S | diS$_D$ | diS$_E$ | triS | |
| Before sulfation | 1.2 | 19.9 | 70.7 | 0.0 | 6.7 | 0.9 | 0.6 | 108 |
| After sulfation | 0.7 | 14.8 | 33.8 | 0.1 | 7.8 | 37.6 | 5.2 | 155 |

As is shown in Table 16, it was confirmed that, by the examination using CSA, the coexistence of a GAG having a sulfate group and a sulfating agent in a strongly basic solution could lead to sulfation of the GAG having a sulfate group and an increase in sulfation degree. In one embodiment, sulfated CSA (i.e., a GAG prepared through sulfation of CSA) is characterized by containing CH-diS$_E$ in the highest disaccharide composition ratio. This characteristic feature is common with chondroitin sulfate E (CSE). Thus, it was also found that the method of the present invention could prepare a CSE-like polysaccharide.

<Example 17> Examination of Sulfation of GAG Having Sulfate Group (2)

2 M aqueous NaOH solution was added to chondroitin sulfate C (CSC) (14.8 kDa) to prepare a solution having a CSC concentration of 200 mg/mL (20% w/v). The solution was heated to 40° C. and TMA-SO$_3$ (2.9 equivalents) was added to the solution. Thereafter, the resultant solution was agitated by means of a stirrer for one hour for sulfation reaction. After the termination of the reaction, the resultant solution was mixed with a three-fold volume of purified water and then dialyzed against purified water for two days. The resultant solution was neutralized by addition of an aqueous NaOH solution and then lyophilized, to thereby yield a dry powder. The resultant sulfated CS was subjected to disaccharide analysis, to thereby calculate the sulfation degree. The results are illustrated in Table 17.

TABLE 17

| | Disaccharide composition ratio (%) | | | | | | | Sulfation degree (%) |
|---|---|---|---|---|---|---|---|---|
| | 0S | 6S | 4S | 2S | diS$_D$ | diS$_E$ | triS | |
| Before sulfation | 0.9 | 65.0 | 13.4 | 0.0 | 16.8 | 0.8 | 3.0 | 123 |
| After sulfation | 0.6 | 50.9 | 7.9 | 0.0 | 22.2 | 13.8 | 4.7 | 145 |

As is shown in Table 17, it was confirmed that, by the examination using CSC, the coexistence of a GAG having a sulfate group and a sulfating agent in a strongly basic solution could lead to sulfation of the GAG having a sulfate group and an increase in sulfation degree. In one embodiment, sulfated CSC (i.e., a GAG prepared through sulfation of CSC) is characterized by containing CH-diS$_D$ in a disaccharide composition ratio of 20% or higher. This characteristic feature is common with chondroitin sulfate D (CSD). Thus, it was also found that the method of the present invention could prepare a CSD-like polysaccharide.

<Example 18> Examination of Sulfation by Use of Solvent Mixture (1)

dCH (8.2 kDa) was mixed with 2 M NaOH solution containing 5% (v/v) dimethylformamide (DMF) to prepare a solution having a CH concentration of 100 mg/mL (10% w/v). The solution was heated to 40° C. and TMA-SO$_3$ (2.9 equivalents) was added to the solution. Thereafter, the resultant solution was agitated by means of a stirrer for one hour for sulfation reaction. After the termination of the reaction, the resultant solution was mixed with a three-fold volume of purified water and then dialyzed against purified water for two days. The resultant solution was neutralized by addition of an aqueous NaOH solution and then lyophilized, to thereby yield a dry powder. The resultant sulfated CH was subjected to disaccharide analysis, to thereby calculate the sulfation degree. The results are illustrated in Table 18.

TABLE 18

| Solvent | Disaccharide composition ratio (%) | | | | | | | Sulfation degree (%) |
|---|---|---|---|---|---|---|---|---|
| | 0S | 6S | 4S | 2S | $diS_D$ | $diS_E$ | triS | |
| 5% DMF/ 2M NaOH | 71.8 | 21.3 | 0.9 | 3.8 | 1.6 | 0.6 | 0.1 | 31 |

As is shown in Table 18, it was confirmed that, by the examination using DMF, a GAG could be sulfated even in the case of use of a solvent mixture containing an organic solvent.

<Example 19> Examination of Sulfation by Use of Solvent Mixture (2)

dCH (8.2 kDa) was mixed with 2 M NaOH solution containing 5% (v/v) organic solvent (dimethyl sulfoxide (DMSO), formamide (FA), pyridine (Pyr), acetonitrile (MeCN), ethanol (EtOH), or tetrahydrofuran (THF)) to prepare a solution having a dCH concentration of 100 mg/mL (10% w/v). The solution was heated to 40° C. and TMA-SO$_3$ (2.9 equivalents) was added to the solution. Thereafter, the resultant solution was agitated by means of a stirrer for three hours for sulfation reaction. After the termination of the reaction, the resultant solution was mixed with a three-fold volume of purified water and then dialyzed against purified water for two days. The resultant solution was neutralized by addition of an aqueous NaOH solution and then lyophilized, to thereby yield a dry powder. The resultant sulfated CH was subjected to disaccharide analysis, to thereby calculate the sulfation degree. The results are illustrated in Table 19.

TABLE 19

| Solvent | Disaccharide composition ratio (%) | | | | | | | Sulfation degree (%) |
|---|---|---|---|---|---|---|---|---|
| | 0S | 6S | 4S | 2S | $diS_D$ | $diS_E$ | triS | |
| 5% DMSO/2M NaOH | 48.6 | 36.0 | 1.4 | 5.2 | 6.0 | 2.3 | 0.6 | 61 |
| 5% FA/2M NaOH | 67.5 | 24.1 | 0.9 | 4.2 | 2.2 | 0.9 | 0.1 | 36 |
| 5% Pyr/2M NaOH | 52.0 | 33.9 | 1.2 | 5.2 | 5.3 | 2.1 | 0.5 | 56 |
| 5% MeCN/2M NaOH | 50.4 | 34.8 | 1.3 | 5.1 | 5.6 | 2.2 | 0.5 | 59 |
| 5% EtOH/2M NaOH | 52.4 | 33.8 | 1.3 | 5.1 | 5.0 | 2.0 | 0.5 | 56 |
| 5% THF/2M NaOH | 49.9 | 35.1 | 1.4 | 5.2 | 5.7 | 2.2 | 0.5 | 59 |

As is shown in Table 19, it was confirmed that a GAG could be sulfated even in the case of use of a solvent mixture containing an organic solvent other than DMF.

<Example 20> Examination of Sulfation by Use of Solvent Mixture (3)

dCH (8.2 kDa) was mixed with 2 M NaOH solution containing 10 to 40% (v/v) organic solvent. (DMSO or EtOH) to prepare a solution having a dCH concentration of 100 mg/mL (10% w/v). The solution was heated to 40° C. and TMA-SO$_3$ (2.9 equivalents) was added to the solution. Thereafter, the resultant solution was agitated by means of a stirrer for three hours for sulfation reaction. After the termination of the reaction, the resultant solution was mixed with a three-fold volume of purified water and then dialyzed against purified water for two days. The resultant solution was neutralized by addition of an aqueous NaOH solution and then lyophilized, to thereby yield a dry powder. The resultant sulfated CH was subjected to disaccharide analysis, to thereby calculate the sulfation degree. The results are illustrated in Table 20.

TABLE 20

| Solvent | Disaccharide composition ratio (%) | | | | | | | Sulfation degree (%) |
|---|---|---|---|---|---|---|---|---|
| | 0S | 6S | 4S | 2S | $diS_D$ | $diS_E$ | triS | |
| 10% DMSO/2M NaOH | 45.2 | 36.1 | 1.8 | 5.8 | 7.4 | 2.8 | 0.9 | 67 |
| 20% DMSO/2M NaOH | 39.4 | 36.4 | 2.4 | 6.3 | 9.6 | 4.0 | 2.0 | 78 |
| 30% DMSO/2M NaOH | 36.4 | 34.5 | 3.0 | 6.8 | 11.2 | 5.0 | 3.1 | 86 |
| 40% DMSO/2M NaOH | 65.1 | 22.2 | 1.8 | 4.0 | 4.0 | 1.9 | 0.9 | 43 |
| 10% EtOH/2M NaOH | 50.4 | 33.6 | 1.6 | 5.7 | 5.9 | 2.2 | 0.6 | 59 |
| 20% EtOH/2M NaOH | 50.7 | 32.1 | 2.0 | 6.0 | 6.1 | 2.3 | 0.8 | 59 |
| 30% EtOH/2M NaOH | 56.4 | 28.6 | 2.1 | 5.8 | 4.7 | 1.8 | 0.6 | 51 |
| 40% EtOH/2M NaOH | 70.0 | 20.8 | 1.7 | 4.4 | 2.0 | 0.8 | 0.2 | 33 |

As is shown in Table 20, it was confirmed that a GAG could be sulfated even in the case of use of a solvent mixture containing an organic solvent. It was also confirmed that appropriate adjustment of the concentration of an organic solvent could lead to production of a sulfated GAG exhibiting a desired sulfation degree. In the case of use of a solvent mixture containing DMSO as an organic solvent, the resultant sulfated glycosaminoglycan exhibited a sulfation degree higher than that in the case of use of a solution not containing DMSO as an organic solvent. Specifically, this tendency was determined in the case of use of a solvent mixture containing 10% to 30% (v/v) DMSO. In the case of use of a solvent mixture containing about 30% (v/v) DMSO, the resultant sulfated glycosaminoglycan exhibited the highest sulfation degree. Thus, it was found that the sulfation method of the present invention preferably involves the use of DMSO as an organic solvent.

<Example 21> Comparison with Conventional Sulfation Method (1)

(1) Sulfation Using Strongly Basic Solution

Na$_2$SO$_4$ and 2 M aqueous NaOH solution were added to CH to prepare a solution having a CH concentration of 66.7 mg/mL (6.67% w/v) and a Na$_2$SO$_4$ concentration of 500 mg/mL. The solution was heated to 40° C. and TMA-SO$_3$ (2.9 equivalents) was added to the solution. Thereafter, the resultant solution was agitated by means of a stirrer for one hour for sulfation reaction. After the termination of the reaction, the resultant solution was mixed with a three-fold volume of purified water and then dialyzed against purified water for two days. The resultant solution was neutralized by addition of an aqueous NaOH solution and then lyophilized, to thereby yield a dry powder.

(2) Sulfation in Organic Solvent

Formamide (FA) was added to CH to prepare a solution having a CH concentration of 200 mg/mL (20% w/v). A sulfur trioxide-triethylamine complex (TEA-$SO_3$) (5 equivalents) was added to the solution, and then the resultant mixture was agitated by means of a stirrer for two hours for sulfation reaction. After the termination of the reaction, the resultant solution was mixed with a three-fold volume of purified water and then dialyzed against purified water for two days. The resultant solution was neutralized by addition of an aqueous NaOH solution and then lyophilized, to thereby yield a dry powder.

The sulfated CHs produced in (1) and (2) above were subjected to disaccharide analysis, to thereby calculate the sulfation degree. The results are illustrated in Table 21.

TABLE 21

| Solvent | Disaccharide composition ratio (%) | | | | | | | Sulfation degree (%) |
|---|---|---|---|---|---|---|---|---|
| | 0S | 6S | 4S | 2S | $diS_D$ | $diS_E$ | triS | |
| 2M NaOH | 65.8 | 26.0 | 0.6 | 4.3 | 2.7 | 0.6 | 0.0 | 38 |
| Formamide (FA) | 63.5 | 32.5 | 0.8 | 2.1 | 0.8 | 0.2 | 0.0 | 37 |

As is shown in Table 21, it was confirmed that the sulfated CH (GAG) produced by the method of the present invention (i.e., sulfation using a strongly basic solution) exhibited a disaccharide composition ratio of CH-2S higher than that of the sulfated CH (GAG) produced by the conventional technique (i.e., sulfation in an organic solvent).

<Example 22> Comparison with Conventional Sulfation Method (2)

(1) Sulfation Using Strongly Basic Solution

2 M aqueous NaOH solution was added to CH to prepare a solution having a CH concentration of 200 mg/mL (20% w/v). The solution was heated to 40° C. and TMA-$SO_3$ (2.9 equivalents) was added to the solution. Thereafter, the resultant solution was agitated by means of a stirrer for one hour for sulfation reaction. After the termination of the reaction, the resultant solution was mixed with a three-fold volume of purified water and then dialyzed against purified water for two days. The resultant solution was neutralized by addition of an aqueous NaOH solution and then lyophilized, to thereby yield a dry powder.

(2) Sulfation in Organic Solvent

Formamide (FA) was added to CH to prepare a solution having a CH concentration of 200 mg/mL (20% w/v). The solution was heated to 40° C. and TEA-$SO_3$ (5 equivalents) was added to the solution. Thereafter, the resultant solution was agitated by means of a stirrer for two hours for sulfation reaction. After the termination of the reaction, the resultant solution was mixed with a three-fold volume of purified water and then dialyzed against purified water for two days. The resultant solution was neutralized by addition of an aqueous NaOH solution and then lyophilized, to thereby yield a dry powder.

The sulfated CHs produced in (1) and (2) above were subjected to disaccharide analysis, to thereby calculate the sulfation degree. The results are illustrated in Table 22.

TABLE 22

| Solvent | Disaccharide composition ratio (%) | | | | | | | Sulfation degree (%) |
|---|---|---|---|---|---|---|---|---|
| | 0S | 6S | 4S | 2S | $diS_D$ | $diS_E$ | triS | |
| 2M NaOH | 27.6 | 42.7 | 1.4 | 7.7 | 16.3 | 2.3 | 2.0 | 95 |
| Formamide (FA) | 22.8 | 60.3 | 0.9 | 2.5 | 10.2 | 3.1 | 0.2 | 91 |

As is shown in Table 22, it was confirmed that the sulfated CH (GAG) produced by the method of the present invention (i.e., sulfation using a strongly basic solution) exhibited a disaccharide composition ratio of CH-2S higher than that of the sulfated CH (GAG) produced by the conventional technique (i.e., sulfation in an organic solvent).

<Example 23> Comparison with Conventional Sulfation Method (3)

(1) Sulfation Using Strongly Basic Solution $Na_2SO_4$ and 2 M aqueous NaOH solution were added to a solution of HA in purified water to prepare a solution having a final HA concentration of 1 mg/mL (0.1% w/v), a final $Na_2SO_4$ concentration of 80 mg/mL, and a final NaOH concentration of 1 M. The solution was cooled to 4° C. and TMA-$SO_3$ (58 equivalents) was added to the solution. Thereafter, the resultant solution was agitated by means of a stirrer for 18 hours for sulfation reaction. After the termination of the reaction, the resultant solution was mixed with a two-fold volume of purified water and then dialyzed against purified water for two days. The resultant solution was neutralized by addition of an aqueous NaOH solution and then lyophilized, to thereby yield a dry powder.

(2) Sulfation in Organic Solvent

N,N-dimethylformamide (DMF) was added to tributylamine (TBA) salt of HA to prepare a solution having an HA concentration of 10 mg/mL (1% w/v). The solution was heated to 60° C. and TMA-$SO_3$ (12 equivalents) was added to the solution. Thereafter, the resultant solution was agitated by means of a stirrer for 48 hours for sulfation reaction. After the termination of the reaction, the resultant solution was mixed with a 2.5-fold volume of acetone and agitated for 30 minutes, and then allowed to stand still for three hours. The precipitate was recovered from the solution and dissolved in purified water to achieve an HA concentration of 8 mg/mL (0.8% w/v), and the solution was dialyzed against purified water for two days. The resultant solution was neutralized by addition of an aqueous NaOH solution and then lyophilized, to thereby yield a dry powder.

The sulfated HAs produced in (1) and (2) above were subjected to disaccharide analysis. The results are illustrated in Table 23.

TABLE 23

| Solvent | Disaccharide composition ratio (%) | | | |
|---|---|---|---|---|
| | 0S | 6S | 4S | 2S |
| 2M NaOH | 64.1 | 20.4 | 12.6 | 3.0 |
| N,N-dimethylformamide (DMF) | 0.1 | 99.9 | 0.0 | 0.0 |

As is shown in Table 23, it was confirmed that the sulfated HA (GAG) produced by the conventional technique (i.e., sulfation in an organic solvent) contained a high disaccharide composition ratio of HA-6S but substantially no HA-4S or HA-2S, whereas the sulfated HA (GAG) produced by the method of the present invention (i.e., sulfation using a strongly basic solution) contained HA-4S and HA-2S, <Example 24> One-Pot Reaction of Deacetylation and Sulfation of Heparosan 2 M aqueous NaOH solution was added to NAH (33.1 kDa) to prepare a solution having an NAH concentration of 40 mg/mL (4% w/v). The solution was heated to 60° C. and agitated by means of a stirrer for four hours for deacetylation reaction. The temperature was changed to 40° C., and TMA-SO$_3$ (7 or 12 equivalents) was added to the solution, followed by agitation by means of a stirrer for 20 hours for sulfation reaction. The resultant solution was neutralized by addition of HCl and then dialyzed against purified water for two days. The resultant solution was neutralized by addition of an aqueous NaOH solution and then lyophilized, to thereby yield a dry powder. The resultant sulfated heparosan was subjected to disaccharide analysis by the method described in <Referential Example 11> above. The results are illustrated in Table 24.

TABLE 24

| Sulfating agent | Disaccharide composition ratio (%) | | | | | | Sulfation degree |
|---|---|---|---|---|---|---|---|
| (Mole equivalents) | 0S | NS | 6S | diS$_1$ | diS$_2$ | triS | (%) |
| 7 | 91.0 | 8.1 | 0.0 | 0.4 | 0.5 | 0.0 | 10 |
| 12 | 51.2 | 26.4 | 2.0 | 7.0 | 9.7 | 3.7 | 73 |

As is shown in Table 24, it was confirmed that, by the examination using NAH, the coexistence of a GAG and a sulfating agent in a strongly basic solution could lead to sulfation of the GAG. It was also found that the deacetylation and sulfation of a GAG could be performed through one-pot procedure in a strongly basic solution.

<Example 25> One-Pot Reaction of Alkylation and Sulfation of Chondroitin (1) Preparation of Methylated Sulfated Chondroitin 2 M aqueous NaOH solution was added to CH to prepare a solution having a CH concentration of 100 mg/mL (10% w/v). The solution was heated to 40° C. and mixed with 0.5-fold volume of iodomethane (CH$_3$I), and then the mixture was agitated by means of a stirrer for two hours for methylation reaction. A portion of the resultant solution was collected as a specimen for determination of the percent introduction a methyl group (i.e., methylation degree). Thereafter, TMA-SO$_3$ (2.9 equivalents) was added to the solution and agitated by means of a stirrer at room temperature for two hours for sulfation reaction. Each of the specimen for determination of methylation degree and the solution after the termination of the reaction was mixed with a three-fold volume of purified water and then dialyzed against purified water for two days. The resultant solution was neutralized by addition of an aqueous NaOH solution and then lyophilized, to thereby yield a dry powder. The resultant methylated chondroitin (i.e., chondroitin before the sulfation reaction) and the methylated sulfated chondroitin were analyzed as described below.

(2) Determination of Methylation Degree

The methylation degree was determined by means of $^1$H-NMR. The methylated chondroitin prepared in (1) above (5 mg) was mixed with heavy water containing 0.01% sodium 3-(trimethylsilyl)propionate-2,2,3,3-d$_4$ (TSP) to prepare a solution. The solution was subjected to $^1$H-NMR, and the integrated value of peaks of signals (2.9 ppm, 3.1 ppm, 3.2 ppm, 3.4 ppm, and 3.5 ppm) corresponding to the methyl group introduced into CH was divided by the integrated value of a peak of a signal (2.0 ppm) corresponding to the acetyl group of a GalNAc residue. The quotient value was expressed in percentage of the methylation degree. Consequently, the methylated chondroitin was found to exhibit a methylation degree of 58%.

(3) Determination of Sulfur Content

The sulfur content was determined by the method described in <Referential Example 12>. Consequently, the methylated sulfated chondroitin prepared in (1) above was found to have a sulfur content of 3.8%.

By the above-described results, it was confirmed that the alkylation and sulfation of a GAG could be performed through one-pot procedure in a strongly basic solution.

<Example 26> Comparison with Conventional Sulfation Method (4)

A solvent was added to CH (5.0 kDa, 28.0 kDa, 30.2 kDa, 32.0 kDa, 35.8 kDa, or 41.8 kDa) to prepare a solution having a CH concentration of 10 to 200 mg/mL (1 to 20% w/v). The solution was heated or cooled to a temperature of 0 to 60° C. and a sulfating agent (TMA-SO$_3$, TEA-SO$_3$, Pyr-SO$_3$, or a sulfur trioxide-N,N-dimethylformamide complex (DMF-SO$_3$)) (0.9 to 10 equivalents) was added to the solution. Thereafter, the resultant solution was agitated by means of a stirrer for 0.5 to 20 hours for sulfation reaction. After the termination of the reaction, the resultant solution was mixed with a three-fold volume of purified water and then dialyzed against purified water for two days. The resultant solution was neutralized by addition of an aqueous NaOH solution and then lyophilized, to thereby yield a dry powder.

In the aforementioned reaction conditions, 0.1 to 2 M aqueous NaOH solution was used as the solvent for the case of the sulfation method of the present invention (i.e., sulfation using a strongly basic solution). In the aforementioned reaction conditions, formamide (FA), N,N-dimethylformamide (DMF), or N-methyl-2-pyrrolidone (NMP) was used as the solvent for the case of a conventional sulfation method (sulfation in an organic solvent).

The sulfated CH prepared as described above was subjected to disaccharide analysis, to thereby calculate the ratio of CH-2S to CH-4S (2S/4S ratio) and the ratio of CH-2S to CH-6S (2S/6S ratio). Table 25 illustrates the results of disaccharide analysis of sulfated CHs (29 samples) prepared by the sulfation method of the present invention, and Table 26 illustrates the results of disaccharide analysis of sulfated CHs (26 samples) prepared by the conventional sulfation method. Table 27 illustrates the results of disaccharide analysis of CSs extracted from animals. In Table 27, chondroitin sulfate A (CSA) was extracted from sturgeon chorda dorsalis, chondroitin sulfate B (CSB) was extracted from pigskin, chondroitin sulfate C (CSC) and chondroitin sulfate D (CSD) were extracted from shark cartilage, and chondroitin sulfate E (CSE) was extracted from squid cartilage.

TABLE 25

| Sample Number | \multicolumn{9}{c}{Disaccharide composition ratio (%)} | | | | | | | | |
|---|---|---|---|---|---|---|---|---|---|
| | 0S | 6S | 4S | 2S | $diS_D$ | $diS_E$ | triS | 2S/4S | 2S/6S |
| B4401 | 74.7 | 19.5 | 0.4 | 3.9 | 1.2 | 0.2 | 0.0 | 9.75 | 0.20 |
| B4402 | 31.6 | 41.4 | 1.3 | 7.9 | 13.7 | 2.2 | 1.9 | 6.08 | 0.19 |
| B4403 | 29.9 | 38.8 | 1.5 | 8.8 | 16.0 | 2.6 | 2.4 | 5.87 | 0.23 |
| B4404 | 35.6 | 36.5 | 1.6 | 9.1 | 13.3 | 2.1 | 1.8 | 5.69 | 0.25 |
| B4201 | 25.3 | 41.0 | 1.4 | 8.1 | 18.2 | 3.0 | 3.0 | 5.79 | 0.20 |
| B4202 | 23.5 | 40.8 | 1.4 | 7.9 | 19.3 | 3.3 | 3.7 | 5.64 | 0.19 |
| B4203 | 22.9 | 40.7 | 1.4 | 7.8 | 19.9 | 3.4 | 3.9 | 5.57 | 0.19 |
| B4204 | 22.6 | 41.1 | 1.4 | 7.9 | 19.8 | 3.4 | 3.8 | 5.64 | 0.19 |
| NA001073-87-05 | 65.8 | 26.0 | 0.6 | 4.3 | 2.7 | 0.6 | 0.0 | 7.17 | 0.17 |
| NA001073-87-06 | 74.1 | 20.3 | 0.5 | 3.4 | 1.4 | 0.3 | 0.0 | 6.80 | 0.17 |
| NA001073-87-07 | 86.0 | 11.2 | 0.3 | 2.0 | 0.4 | 0.1 | 0.0 | 6.67 | 0.18 |
| NA001073-87-08 | 93.9 | 5.0 | 0.1 | 0.9 | 0.1 | 0.0 | 0.0 | 9.00 | 0.18 |
| B4601 | 98.1 | 1.3 | 0.1 | 0.5 | 0.0 | 0.0 | 0.0 | 5.00 | 0.38 |
| B4602 | 70.6 | 16.4 | 1.2 | 8.2 | 3.0 | 0.5 | 0.2 | 6.83 | 0.50 |
| B4001 | 18.8 | 40.4 | 1.6 | 7.0 | 22.2 | 4.2 | 5.8 | 4.38 | 0.17 |
| B4002 | 27.7 | 42.0 | 1.6 | 7.4 | 15.6 | 3.1 | 2.6 | 4.63 | 0.18 |
| B4003 | 63.0 | 28.1 | 1.2 | 4.2 | 2.6 | 0.7 | 0.3 | 3.50 | 0.15 |
| NA001073-86-01 | 96.4 | 3.0 | 0.1 | 0.6 | 0.0 | 0.0 | 0.0 | 6.00 | 0.20 |
| NA001073-86-02 | 87.8 | 10.1 | 0.2 | 1.9 | 0.0 | 0.0 | 0.0 | 9.50 | 0.19 |
| NA001073-86-03 | 75.0 | 19.6 | 0.4 | 3.6 | 1.2 | 0.2 | 0.0 | 9.00 | 0.18 |
| NA001073-86-04 | 64.7 | 26.9 | 0.6 | 4.7 | 2.7 | 0.4 | 0.0 | 7.83 | 0.17 |
| NA001073-86-05 | 57.0 | 31.9 | 0.8 | 5.4 | 4.3 | 0.7 | 0.0 | 6.75 | 0.17 |
| NA001073-86-06 | 54.4 | 33.2 | 0.9 | 5.4 | 5.1 | 1.0 | 0.0 | 6.00 | 0.16 |
| NA001073-86-07 | 60.4 | 29.1 | 0.9 | 4.8 | 3.9 | 1.0 | 0.0 | 5.33 | 0.16 |
| NA001073-86-08 | 62.6 | 27.9 | 1.0 | 4.6 | 3.1 | 0.9 | 0.0 | 4.60 | 0.16 |
| B4501 | 27.1 | 40.6 | 1.5 | 8.2 | 17.1 | 2.8 | 2.7 | 5.47 | 0.20 |
| B4502 | 25.6 | 41.4 | 1.5 | 8.1 | 17.8 | 2.9 | 2.8 | 5.40 | 0.20 |
| B4503 | 26.0 | 41.7 | 1.5 | 7.9 | 17.6 | 2.8 | 2.6 | 5.27 | 0.19 |
| B4504 | 27.5 | 42.8 | 1.4 | 7.7 | 16.3 | 2.3 | 2.0 | 5.50 | 0.18 |

TABLE 26

| Sample Number | \multicolumn{9}{c}{Disaccharide composition ratio (%)} | | | | | | | | |
|---|---|---|---|---|---|---|---|---|---|
| | 0S | 6S | 4S | 2S | $diS_D$ | $diS_E$ | triS | 2S/4S | 2S/6S |
| 18401 | 18.6 | 63.7 | 1.4 | 2.3 | 9.7 | 4.2 | 0.0 | 1.64 | 0.04 |
| 18601 | 9.9 | 69.5 | 1.0 | 1.7 | 15.6 | 2.3 | 0.0 | 1.70 | 0.02 |
| 19301 | 13.1 | 65.4 | 1.2 | 1.7 | 13.1 | 5.5 | 0.0 | 1.42 | 0.03 |
| 19501 | 16.7 | 64.0 | 1.4 | 2.0 | 11.3 | 4.6 | 0.0 | 1.43 | 0.03 |
| 19601 | 19.1 | 64.3 | 0.9 | 1.8 | 9.7 | 4.3 | 0.0 | 2.00 | 0.03 |
| B101 | 35.1 | 56.7 | 0.0 | 0.2 | 5.5 | 2.3 | 0.0 | | 0.00 |
| B301 | 34.3 | 55.0 | 0.0 | 2.7 | 5.9 | 2.1 | 0.0 | | 0.05 |
| B601 | 32.2 | 55.5 | 1.7 | 2.4 | 5.7 | 2.6 | 0.0 | 1.41 | 0.04 |
| B1601 | 23.1 | 61.8 | 1.3 | 2.2 | 8.2 | 3.4 | 0.0 | 1.69 | 0.04 |
| B1904 | 15.5 | 64.2 | 1.3 | 2.1 | 11.7 | 5.0 | 0.3 | 1.62 | 0.03 |
| 8701 | 63.5 | 32.5 | 0.8 | 2.1 | 0.8 | 0.2 | 0.0 | 2.63 | 0.06 |
| 8702 | 20.8 | 64.2 | 1.0 | 2.6 | 8.4 | 2.7 | 0.2 | 2.60 | 0.04 |
| NA6101 | 22.8 | 60.3 | 0.9 | 2.5 | 10.2 | 3.1 | 0.2 | 2.78 | 0.04 |
| NA6001 | 17.3 | 63.1 | 0.8 | 2.3 | 12.3 | 3.8 | 0.3 | 2.88 | 0.04 |
| 12701 | 6.3 | 61.6 | 0.9 | 1.7 | 16.8 | 8.8 | 3.9 | 1.89 | 0.03 |
| 12706 | 90.2 | 8.4 | 0.6 | 0.7 | 0.0 | 0.0 | 0.0 | 1.17 | 0.08 |
| 11404 | 14.4 | 60.6 | 2.0 | 2.4 | 11.8 | 6.3 | 2.4 | 1.20 | 0.04 |
| 12703 | 61.2 | 33.0 | 1.7 | 2.4 | 1.1 | 0.6 | 0.0 | 1.41 | 0.07 |
| 12704 | 69.4 | 26.3 | 1.4 | 2.0 | 0.6 | 0.3 | 0.0 | 1.43 | 0.08 |
| 12705 | 78.9 | 17.8 | 1.5 | 1.4 | 0.3 | 0.1 | 0.0 | 0.93 | 0.08 |
| 11308 | 86.1 | 11.8 | 0.8 | 1.0 | 0.2 | 0.1 | 0.0 | 1.25 | 0.08 |
| 11309 | 92.9 | 6.0 | 0.4 | 0.6 | 0.0 | 0.0 | 0.0 | 1.50 | 0.10 |
| 7701 | 93.4 | 6.2 | 0.1 | 0.0 | 0.2 | 0.0 | 0.0 | 0.00 | 0.00 |
| 6703A2 | 85.2 | 6.1 | 0.1 | 0.0 | 1.2 | 2.3 | 5.1 | 0.00 | 0.00 |
| 7101 | 93.7 | 5.8 | 0.1 | 0.0 | 0.3 | 0.1 | 0.0 | 0.00 | 0.00 |
| 7102 | 95.6 | 4.4 | 0.0 | 0.0 | 0.0 | 0.0 | 0.0 | | 0.00 |

TABLE 27

| Sample Name | \multicolumn{10}{c}{Disaccharide composition ratio (%)} | | | | | | | | | |
|---|---|---|---|---|---|---|---|---|---|---|
| | 0S | 6S | 4S | 2S | $diS_D$ | $diS_E$ | $diS_B$ | triS | 2S/4S | 2S/6S |
| CSA | 1.1 | 5.9 | 93.0 | 0.0 | 0.0 | 0.0 | 0.0 | 0.0 | 0.00 | 0.00 |
| CSB | 1.1 | 2.1 | 89.6 | 0.0 | 0.0 | 0.0 | 7.3 | 0.0 | 0.00 | 0.00 |
| CSC | 1.3 | 70.9 | 18.7 | 0.0 | 8.2 | 0.9 | 0.0 | 0.0 | 0.00 | 0.00 |
| CSD | 1.0 | 35.5 | 41.9 | 0.0 | 20.9 | 0.7 | 0.0 | 0.0 | 0.00 | 0.00 |
| CSE | 3.8 | 9.9 | 23.7 | 0.0 | 0.0 | 62.6 | 0.0 | 0.0 | 0.00 | 0.00 |

As is shown in Table 25, it was confirmed that the sulfated CH prepared by the sulfation method of the present invention exhibited a 2S/4S ratio of 3.50 to 9.75 and a 2S/6S ratio of 0.15 to 0.50. As is shown in Table 26, it was confirmed that the sulfated CH prepared by the conventional sulfation method exhibited a 2S/4S ratio of 0.00 to 3.00 and a 2S/6S ratio of 0.00 to 0.10. As is shown in Table 27, it was confirmed that no CH-2S was detected in CS extracted from an animal (i.e., naturally occurring CS), and the animal-derived CS exhibited a 2S/4S ratio of 0.00 and a 2S/6S ratio of 0.00.

<Example 27> Sulfation of Low-Molecular-Weight Hyaluronic Acid

2 M aqueous NaOH solution was added to HA (20 kDa or 100 kDa) to prepare a solution having an HA concentration of 50 mg/mL (5% w/v). The solution was cooled to 4° C. and TMA-SO$_3$ (8.7 equivalents) was added to the solution. Thereafter, the resultant solution was agitated by means of a stirrer for 24 hours for sulfation reaction. After the termination of the reaction, the resultant solution was mixed with a two-fold volume of purified water and then dialyzed against purified water for two days. The resultant solution was neutralized by addition of an aqueous NaOH solution and then lyophilized, to thereby yield a dry powder. The sulfation degree of the resultant sulfated HA was determined, to thereby calculate the sulfur content. The results are illustrated in Table 28.

TABLE 28

| Sample | Sulfation degree (%) | Sulfur content (%) |
|---|---|---|
| HA (20 kDa) | 67 | 5.0 |
| HA (100 kDa) | 66 | 4.9 |

As is shown in Table 28, it was confirmed that the sulfation method of the present invention could be applied not only to sulfation of high-molecular-weight HA, but also to sulfation of low-molecular-weight HA (molecular weight: 100 kDa or lower).

<Example 28> Preparation of Sulfated Heparosan (1)

(1) Deacetylation of Heparosan

2 M aqueous NaOH solution was added to NAH (33.1 kDa) to prepare a solution having an NAH concentration of 100 mg/mL (10% w/v). The solution was heated to 60° C. and agitated by means of a stirrer for four hours for deacetylation reaction. The solution was neutralized by addition of $H_2SO_4$ and then dialyzed against purified water for two days. The resultant solution was neutralized by addition of an aqueous NaOH solution and then lyophilized, to thereby yield a dry powder. Thus, deacetylated HPN was prepared.

(2) Sulfation of Deacetylated Heparosan

The deacetylated HPN prepared in (1) above was mixed with 2 M NaOH solution containing 20% (v/v) DMSO to prepare a solution having a deacetylated HPN concentration of 50 mg/mL (5% w/v). The solution was heated to 40° C. and TMA-$SO_3$ (18 equivalents) was added to the solution. Thereafter, the resultant solution was agitated by means of a stirrer for 20 hours for sulfation reaction. After the termination of the reaction, the resultant solution was mixed with a two-fold volume of purified water and then dialyzed against purified water for two days. The resultant solution was neutralized by addition of an aqueous NaOH solution and then lyophilized, to thereby yield a dry powder.

The sulfated HPN prepared in (2) above was subjected to disaccharide analysis. The results are illustrated in Table 29.

TABLE 29

| Disaccharide composition ratio (%) | | | | | | | | Sulfation degree (%) |
| --- | --- | --- | --- | --- | --- | --- | --- | --- |
| 0S | NS | 6S | 2S | $diS_1$ | $diS_2$ | $diS_3$ | triS | |
| 5.5 | 39.7 | 1.8 | 0.0 | 15.4 | 24.0 | 0.0 | 13.5 | 161 |

<Example 29> Determination of Anticoagulant Activity of Sulfated Heparosan

HEP and the sulfated HPN prepared in Example 28 (samples for analysis) were determined for activated partial thromboplastin time (APTT) by the method described below.

Blood was collected from an SD male rat by means of a Venoject II vacuum blood-collecting tube (containing 3.2% sodium citrate, manufactured by TERUMO CORPORATION), and plasma was obtained from the blood. The plasma (225 µL) was mixed with a solution of a specimen (sulfated NAH or HEP) in distilled water (0.1 mg/mL) (25 µL) to prepare a specimen for analysis. Separately, the plasma (225 µL) was mixed with distilled water (25 µL) to prepare a negative control. The APTT was determined by means of a full-automatic blood coagulation fibrinolysis measuring device STA Compact (manufactured by Roche Diagnostics), and the test was performed by the method described in the attached instruction.

The results are illustrated in Table 30.

TABLE 30

| Sample | APTT (sec) |
| --- | --- |
| Distilled water (negative control) | 28.4 |
| HEP | 121.0 |
| Sulfated HPN | 122.6 |

As is shown in Table 30, it was confirmed that the sulfated HPN prepared in Example 28 exhibited an APTT comparable to that of HEP. Thus, it was found that the sulfated GAG prepared by the sulfation method of the present invention, in one embodiment, exhibited heparin-like anticoagulant activity.

<Example 30> Preparation of Sulfated Heparosan (2)

(1) Preparation of Epimerized Heparosan

NAH (33.1 kDa) was subjected to epimerization reaction by the method described in the document (WO 2014/200045), to thereby prepare epimerized HPN (EpHPN) wherein GlcA residues in NAH were partially epimerized with IdoA residues. The EpHPN was found to have an IdoA content of 32.8%.

(2) Deacetylation and Sulfation of Epimerized Heparosan

In place of NAH, the EpHPN prepared in (1) above was subjected to deacetylation and sulfation by the method described in Example 28.

The sulfated EpHPN prepared in (2) above was subjected to disaccharide analysis. The results are illustrated in Table 31.

TABLE 31

| Disaccharide composition ratio (%) | | | | | | | | Sulfation degree (%) |
| --- | --- | --- | --- | --- | --- | --- | --- | --- |
| 0S | NS | 6S | 2S | $diS_1$ | $diS_2$ | $diS_3$ | triS | |
| 13.6 | 44.7 | 3.5 | 0.0 | 11.4 | 15.9 | 0.0 | 10.8 | 135 |

As is shown in Table 31, it was confirmed that the sulfation method of the present invention could be applied not only to sulfation of a GAG having only a GlcA residue as a HexA residue, but also to sulfation of a GAG having an IdoA residue. The present inventors have found that the aforementioned sulfated EpNAH is a GAG exhibiting heparin-like anticoagulant activity similar to that of the sulfated NAH described in Example 28. Thus, it was found that the method of the present in could prepare a GAG having a composition and characteristics similar to those of HPN, which is a sulfated polysaccharide having a GlcN residue as a HexN residue and GlcA and IdoA residues as HexA residues and exhibiting anticoagulant activity.

<Example 31> Preparation of Sulfated Chondroitin (1)

An aqueous NaOH solution (2 M to 4 M) was added to CH (113 kDa) to prepare a solution having a CH concentration of 50 mg/mL (5% w/v). The solution was cooled to 4° C. and TMA-$SO_3$ (14.5 equivalents) was added to the solution. Thereafter, the resultant solution was agitated by means of a stirrer for 24 hours for sulfation reaction. After the termination of the reaction, the resultant solution was mixed with a three-fold volume of purified water and then dialyzed against purified water for two days. The resultant solution was neutralized by addition of an aqueous NaOH solution and then lyophilized, to thereby yield a dry powder. The resultant sulfated CH was subjected to disaccharide analysis, to thereby calculate the sulfation degree. The results are illustrated in Table 32.

TABLE 32

| NaOH | Disaccharide composition ratio (%) | | | | | | | Sulfation degree |
|---|---|---|---|---|---|---|---|---|
| (M) | 0S | 6S | 4S | 2S | $diS_D$ | $diS_E$ | triS | (%) |
| 2 | 8.9 | 49.2 | 0.3 | 6.6 | 30.5 | 2.9 | 1.7 | 128 |
| 3 | 5.0 | 46.0 | 0.3 | 4.0 | 35.6 | 4.6 | 4.6 | 145 |
| 4 | 4.0 | 47.7 | 0.3 | 3.4 | 36.6 | 4.3 | 3.8 | 145 |

<Example 32> Preparation of Sulfated Chondroitin (2)

2 M aqueous NaOH solution was added to CH (113 kDa) to prepare a solution having a CH concentration of 50 mg/mL (5% w/v). The solution was cooled to 4° C. and TMA-SO$_3$ (8.7 equivalents) was added to the solution. Thereafter, the resultant solution was agitated by means of a stirrer for 24 hours for sulfation reaction. The sulfation reaction solution was found to have a pH of 13.8 as measured at the time of completion of the reaction (i.e., 24 hours after addition of the sulfating agent). After the termination of the reaction, the resultant solution was mixed with a three-fold volume of purified water and then dialyzed against purified water for two days. The resultant solution was neutralized by addition of an aqueous NaOH solution and then lyophilized, to thereby yield a dry powder.

The dry powder was again subjected to sulfation reaction under the same conditions as described above, to thereby yield a dry powder. The resultant sulfated CH was subjected to disaccharide analysis, to thereby calculate the sulfation degree. The results are illustrated in Table 33.

TABLE 33

| Disaccharide composition ratio (%) | | | | | | | Sulfation degree |
|---|---|---|---|---|---|---|---|
| 0S | 6S | 4S | 2S | $diS_D$ | $diS_E$ | triS | (%) |
| 1.9 | 45.6 | 0.1 | 2.4 | 40.7 | 4.7 | 4.6 | 153 |

<Example 33> Preparation of Sulfated Chondroitin (3)

2 M aqueous NaOH solution was added to CH (27 kDa) to prepare a solution having a CH concentration of 50 mg/mL (5% w/v). The solution was cooled to 4° C. and TMA-SO$_3$ (8.7 equivalents) was added to the solution. Thereafter, the resultant solution was agitated by means of a stirrer for 24 hours for sulfation reaction. After the termination of the reaction, the resultant solution was mixed with a three-fold volume of purified water and then dialyzed against purified water for two days. The resultant solution was neutralized by addition of an aqueous NaOH solution and then lyophilized, to thereby yield a dry powder.

The dry powder was again subjected to sulfation reaction under the same conditions as described above, to thereby yield a dry powder. The dry powder was again subjected to sulfation reaction under the same conditions as described above, to thereby yield a dry powder. The resultant sulfated CH was subjected to disaccharide analysis, to thereby calculate the sulfation degree. The results are illustrated in Table 34.

TABLE 34

| Disaccharide composition ratio (%) | | | | | | | Sulfation degree |
|---|---|---|---|---|---|---|---|
| 0S | 6S | 4S | 2S | $diS_D$ | $diS_E$ | triS | (%) |
| 0.6 | 32.9 | 0.1 | 0.6 | 49.1 | 7.0 | 9.8 | 175 |

As is shown in Tables 32 to 34, sulfated CH (i.e., a GAG prepared through sulfation of CH) is characterized by, in one embodiment, containing CH-diS$_D$ in a disaccharide composition ratio of 20% or higher. This characteristic feature is common with chondroitin sulfate D (CSD). Thus, it was found that the method of the present invention could prepare a CSD-like polysaccharide.

<Example 34> Comparison with Conventional Sulfation Method (5)

(1) Sulfation Using Strongly Basic Solution

Na$_2$SO$_4$ and 2 M aqueous NaOH solution were added to a solution of HA in purified water to prepare a solution having final HA concentration of 10 mg/mL (1% w/v), a final Na$_2$SO$_4$ concentration of 80 mg/mL, and a final NaOH concentration of 1 M. The solution was cooled to 4° C. and TMA-SO$_3$ (58 equivalents) was added to the solution. Thereafter, the resultant solution was agitated by means of a stirrer for 18 hours for sulfation reaction. After the termination of the reaction, the resultant solution was mixed with a two-fold volume of purified water and then dialyzed against purified water for two days. The resultant solution was neutralized by addition of an aqueous NaOH solution and then lyophilized, to thereby yield a dry powder. The resultant sulfated hyaluronic acid was found to have a sulfur content of 2.9%.

(2) Sulfation in Organic Solvent

N,N-dimethylformamide (DMF) was added to tributylamine (TBA) salt of HA to prepare a solution having an HA concentration of 1 mg/mL (0.1% w/v). The solution was heated to 40° C. and mixed with Pyr-SO$_3$ (1 equivalent). Thereafter, the resultant mixture was agitated by means of a stirrer for three hours for sulfation reaction. After the termination of the reaction, the resultant solution was mixed with an equiamount of purified water and then dialyzed against purified water for two days. The resultant solution was neutralized by addition of an aqueous NaOH solution and then lyophilized, to thereby yield a dry powder. The resultant sulfated hyaluronic acid was found to have a sulfur content of 3.0%.

(3) Determination of Sulfate Group by NMR

Figure 2:
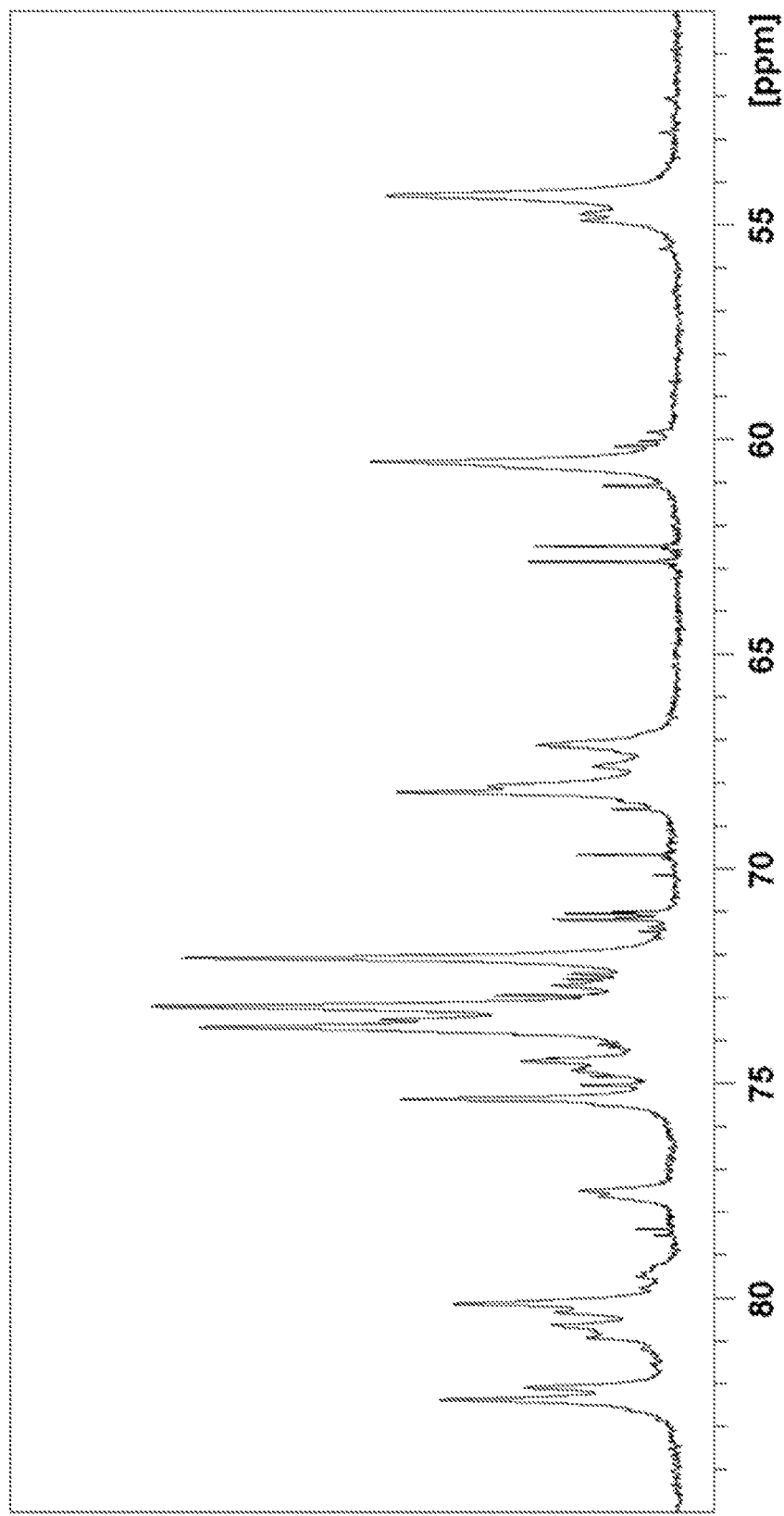
FIG. 2 A chart illustrating the results of $^{13}$C-NMR analysis of sulfated hyaluronic acid prepared by a sulfation method using a strongly basic solution.
Figure 3:
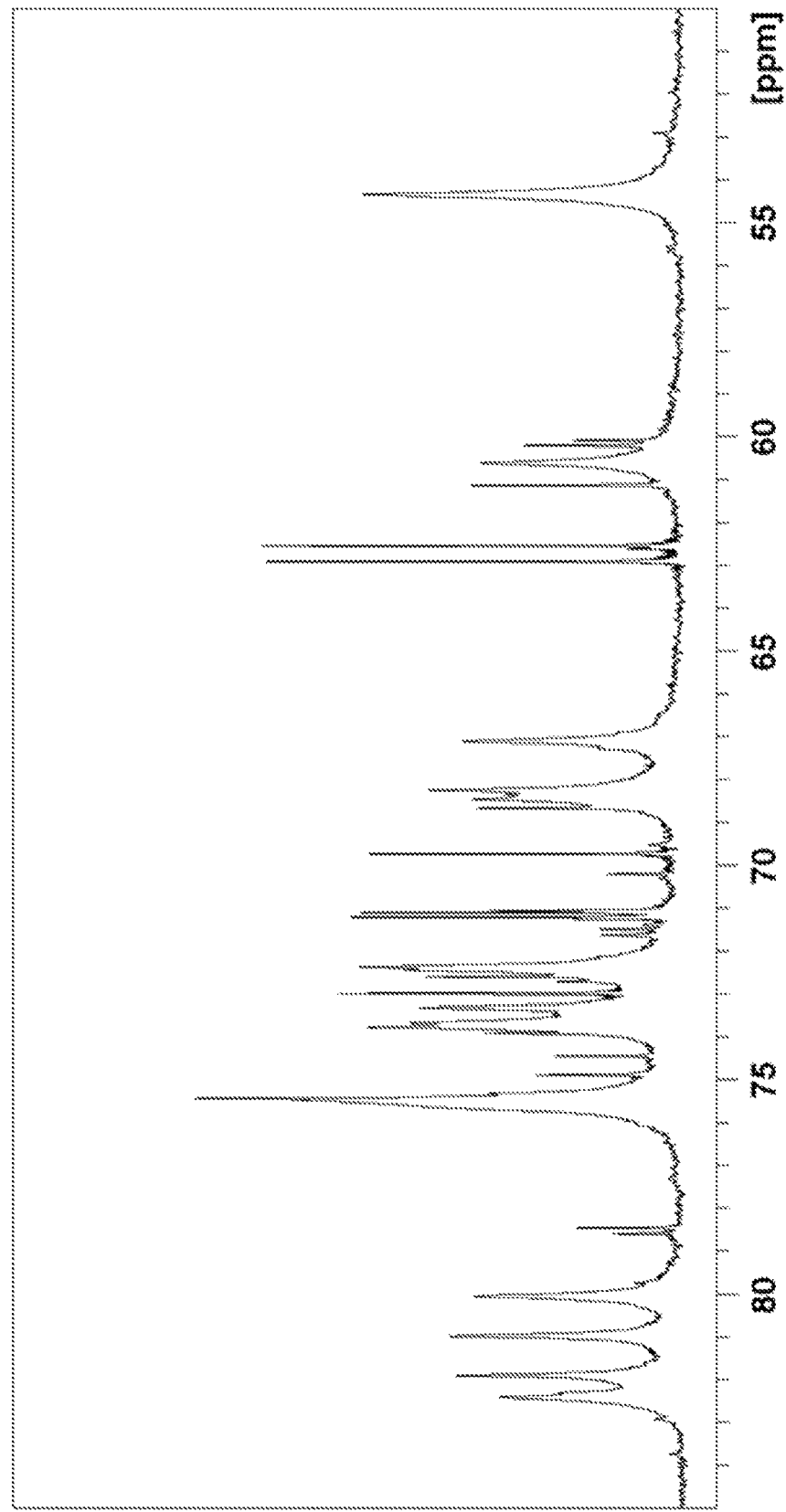
FIG. 3 A chart illustrating the results of $^{13}$C-NMR analysis of sulfated hyaluronic acid prepared by a sulfation method using an organic solvent.

A sulfate group was determined by means of $^{13}$C-NMR. The above-prepared sulfated hyaluronic acid (5 mg) was mixed with heavy water containing 0.01% tetramethylsilane (TMS) to thereby prepare a solution. The solution was subjected to $^{13}$C-NMR for determining the presence of a signal (77.5 ppm) corresponding to a 4-O-sulfate group in a GlcNAc residue. FIG. 2 illustrates the results of analysis of the sulfated hyaluronic acid produced by the sulfation method of the present invention. FIG. 3 illustrates the results of analysis of the sulfated hyaluronic acid produced by the conventional sulfation method.

As is shown in FIG. 2, the sulfated hyaluronic acid produced by the sulfation method of the present invention exhibits a signal at 77.5 ppm; i.e., the presence of a 4-O-sulfate group in a GlcNAc residue. In contrast, as is shown in FIG. 3, the sulfated hyaluronic acid produced by the conventional sulfation method exhibits no signal at 77.5 ppm; i.e., the absence of a 4-O-sulfate group in a GlcNAc residue.

INDUSTRIAL APPLICABILITY

According to the present invention, a GAG can be sulfated in a solution of a non-organic solvent, and thus a sulfated GAG can be produced in the solution.

Japanese Patent Application No. 2015-073148 (filing date: Mar. 31, 2015) is incorporated herein by reference in its entirety. All publications, patent applications, and technical standards mentioned in this specification are incorporated herein by reference to the same extent as if each individual publication, patent application, or technical standard was specifically and individually indicated to be incorporated by reference.

The invention claimed is:

1. A method for sulfating a glycosaminoglycan, the method comprising performing sulfation reaction in a strongly basic solution under coexistence of a glycosaminoglycan with a sulfating agent, wherein the pH of the strongly basic solution is set to be 11.5 or higher.

2. The method according to claim 1, wherein the glycosaminoglycan is selected from among the following glycosaminoglycans (A) to (D):
   (A) a glycosaminoglycan having a hexuronic acid residue;
   (B) a glycosaminoglycan prepared through addition or elimination of a substituent or a functional group to or from the glycosaminoglycan (A);
   (C) a glycosaminoglycan prepared through deacetylation of the glycosaminoglycan (A); and
   (D) a glycosaminoglycan prepared through alkylation of the glycosaminoglycan (A).

3. A method for producing a sulfated glycosaminoglycan, the method comprising performing sulfation reaction in a strongly basic solution under coexistence of a glycosaminoglycan with a sulfating agent, wherein the pH of the strongly basic solution is set to be 11.5 or higher.

4. The method according to claim 3, the method further comprising a step of performing deacetylation reaction of the glycosaminoglycan.

5. The method according to claim 3, the method further comprising a step of performing alkylation reaction of the glycosaminoglycan.

6. The method according to claim 3, wherein the sulfated glycosaminoglycan has heparin-like anticoagulant activity.

7. The method according to claim 3, wherein the sulfated glycosaminoglycan is sulfated heparosan having heparin-like anticoagulant activity.

8. The method according to claim 3, wherein the sulfated glycosaminoglycan is chondroitin sulfate containing 3 mol % or higher of a disaccharide having a structure represented by the following formula as the composition ratio of disaccharide units:

[HexA(2S)1-3GalN1-4]

(where "HexA" represents a hexuronic acid residue; "GalN" represents a galactosamine residue; "1-3" represents a 1-3 glycosidic bond; "1-4" represents a 1-4 glycosidic bond; and "2S" represents a 2-O-sulfate group, respectively).

9. The method according to claim 3, wherein the sulfated glycosaminoglycan is chondroitin sulfate containing a disaccharide having a structure represented by the following formula (b) over 3 times as many as a disaccharide having a structure represented by the following formula (a):

[HexA1-3GalN(4S)1-4]   (a)

[HexA(2S)1-3GalN1-4]   (b)

(where "HexA" represents a hexuronic acid residue; "GalN" represents a galactosamine residue; "1-3" represents a 1-3 glycosidic bond; "1-4" represents a 1-4 glycosidic bond; "4S" represents a 4-O-sulfate group; and "2S" represents a 2-O-sulfate group, respectively).

10. The method according to claim 3, wherein the sulfated glycosaminoglycan is chondroitin sulfate containing a disaccharide having a structure represented by the following formula (d) over 0.1 times as many as a disaccharide having a structure represented by the following formula (c):

[HexA1-3GalN(6S)1-4]   (c)

[HexA(2S)1-3GalN1-4]   (d)

(where "HexA" represents a hexuronic acid residue; "GalN" represents a galactosamine residue; "1-3" represents a 1-3 glycosidic bond; "1-4" represents a 1-4 glycosidic bond; "6S" represents a 6-O-sulfate group; and "2S" represents a 2-O-sulfate group, respectively).

11. The method according to claim 3, wherein the sulfated glycosaminoglycan is chondroitin sulfate having 25 mol % or higher of a disaccharide having a structure represented by the following formula as the composition ratio of disaccharide units:

[HexA(2S)1-3GalN(6S)1-4]

(where "HexA" represents a hexuronic acid residue; "GalN" represents a galactosamine residue; "1-3" represents a 1-3 glycosidic bond; "1-4" represents a 1-4 glycosidic bond; "2S" represents a 2-O-sulfate group; and "6S" represents a 6-O-sulfate group, respectively).

12. The method according to claim 3, wherein the sulfated glycosaminoglycan is sulfated hyaluronic acid containing a disaccharide having a structure represented by the following formula as the disaccharide composition:

[HexA1-3GlcN(4S)1-4]

(where "HexA" represents a hexuronic acid residue; "GlcN" represents a glucosamine residue; "1-3" represents a 1-3 glycosidic bond; "1-4" represents a 1-4 glycosidic bond; and "4S" represents a 4-O-sulfate group, respectively).

13. The method according to claim 3, wherein the sulfated glycosaminoglycan is sulfated hyaluronic acid having the following characteristics (A) and (B):
   (A) a molecular weight of 2,000,000 Da or higher, and
   (B) a sulfur content of 2 mass % or higher.

* * * * *

UNITED STATES PATENT AND TRADEMARK OFFICE
CERTIFICATE OF CORRECTION

PATENT NO. : 10,259,889 B2
APPLICATION NO. : 15/563196
DATED : April 16, 2019
INVENTOR(S) : Toshikazu Minamisawa et al.

It is certified that error appears in the above-identified patent and that said Letters Patent is hereby corrected as shown below:

On the Title Page

Column 2, item (57) under Abstract, Line 1; After "is" insert -- to --

In the Specification

Column 1, Background Art, Line 33 (Approx.); Delete "hex conic" and insert -- hexuronic --, therefor Column 1, Background Art, Line 59 (Approx.); Delete "ΔHexA (2S)" and insert -- ΔHexA(2S) --, therefor Column 1, Background Art, Line 62 (Approx.); Delete "(65)" and insert -- (6S) --, therefor Column 1, Background Art, Line 64 (Approx.); Delete "(NS, 6S)" and insert -- (NS,6S) --, therefor Column 3, Summary of the Invention, Line 12 (Approx.); After "is" insert -- to --

Column 5, Means for Solving the Invention, Line 34 (Approx.); Delete "solvent," and insert -- solvent. --, therefor Column 5, Means for Solving the Invention, Line 40; Delete "C:" and insert -- CH --, therefor Column 7, Modes for Carrying out the Invention, Line 4; After "lower," insert -- or --

Column 7, Modes for Carrying out the Invention, Line 41; After "use" insert -- of --

Column 11, Modes for Carrying out the Invention, Line 22; Delete "addition" and insert -- additional --, therefor Column 12, Modes for Carrying out the Invention, Line 1; Delete "1%," and insert -- 1%. --, therefor Signed and Sealed this
Thirteenth Day of August, 2019

Andrei Iancu
*Director of the United States Patent and Trademark Office*

CERTIFICATE OF CORRECTION (continued)
U.S. Pat. No. 10,259,889 B2

Column 12, Modes for Carrying out the Invention, Line 64; Delete "20%," and insert -- 20%. --, therefor Column 13, Modes for Carrying out the Invention, Line 56; Delete "except," and insert -- except --, therefor Column 16, Modes for Carrying out the Invention, Line 35; After "method" insert -- . --

Column 18, Modes for Carrying out the Invention, Line 14 (Approx.); Delete "perform" and insert -- performing --, therefor Column 19, Modes for Carrying out the Invention, Line 37; Delete "minutes longer," and insert -- minutes or longer, --, therefor Column 21, Modes for Carrying out the Invention, Line 26; Delete "1>" and insert -- 11> --, therefor Column 21, Modes for Carrying out the Invention, Line 40; Delete "[HexA-" and insert -- [HexA1- --, therefor Column 21, Modes for Carrying out the Invention, Line 40; After ""CH-4S";" insert -- a --

Column 21, Modes for Carrying out the Invention, Line 48; Delete ""CH-diS$_3$";" and insert -- "CH-diS$_B$"; --, therefor Column 23, Modes for Carrying out the Invention, Line 32; Delete "CH-diS$_3$" and insert -- CH-diS$_B$ --, therefor Column 24, Modes for Carrying out the Invention, Line 14; Delete "$\Delta$Di-diS$_3$;" and insert -- $\Delta$Di-diS$_B$; --, therefor Column 25, Modes for Carrying out the Invention, Line 41; Delete "sulfat ion" and insert -- sulfation --, therefor Column 26, Modes for Carrying out the Invention, Line 56; Delete "HS diS$_2$," and insert -- HS-diS$_2$, --, therefor Column 28, Modes for Carrying out the Invention, Line 21; Delete "Chem," and insert -- Chem. --, therefor Column 28, Modes for Carrying out the Invention, Line 65; Delete "TSK gel" and insert -- TSKgel --, therefor Column 29, Modes for Carrying out the Invention, Line 12; Delete "SEIKAGAKU  CORPORATION" and insert -- SEIKAGAKU CORPORATION --, therefor

CERTIFICATE OF CORRECTION (continued)
U.S. Pat. No. 10,259,889 B2

Column 29, Modes for Carrying out the Invention, Line 54; Delete "[θ]=" and insert -- [η]= --, therefor Column 30, Modes for Carrying out the Invention, Line 9; Delete "by," and insert -- by --, therefor Column 30, Modes for Carrying out the Invention, Line 27; Delete "acetonitrdle)," and insert -- acetonitrile), --, therefor Column 44, Modes for Carrying out the Invention, Line 64; Delete "dimethylformamide" and insert -- N,N-dimethylformamide --, therefor Column 49, Modes for Carrying out the Invention, Line 55; After "introduction" insert -- of --

Column 54, Modes for Carrying out the Invention, Line 44; Delete "in" and insert -- invention --, therefor Column 56, Modes for Carrying out the Invention, Line 24 (Approx.); After "having" insert -- a --